US012796734B2

(12) United States Patent
Tang et al.

(10) Patent No.: US 12,796,734 B2
(45) Date of Patent: Nov. 17, 2026

(54) ATOMIZER AND AIR OUTPUT CHANNEL PLUG-IN USED BY SAME, AND ELECTRONIC ATOMIZATION DEVICE

(71) Applicant: SHENZHEN SMOORE TECHNOLOGY LIMITED, Shenzhen (CN)

(72) Inventors: Guangwu Tang, Shenzhen (CN); Yu Wang, Shenzhen (CN); Chengzhi Yang, Shenzhen (CN); Kaicheng Wang, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 1126 days.

(21) Appl. No.: 17/820,939

(22) Filed: Aug. 19, 2022

(65) Prior Publication Data

US 2022/0400761 A1 Dec. 22, 2022

Related U.S. Application Data

(63) Continuation of application No. PCT/CN2020/114886, filed on Sep. 11, 2020.

(30) Foreign Application Priority Data

Feb. 20, 2020 (CN) ......................... 202010105137.9
Aug. 24, 2020 (WO) ................ PCT/CN2020/110870

(51) Int. Cl.
*A24F 40/40* (2020.01)
*A24F 7/00* (2006.01)
(Continued)

(52) U.S. Cl.
CPC ................ *A24F 40/40* (2020.01); *A24F 7/00* (2013.01); *A24F 40/10* (2020.01); *A24F 40/48* (2020.01);
(Continued)

(58) Field of Classification Search
CPC .. A24F 40/40; A24F 7/00; A24F 40/10; A24F 40/48; A24F 40/485; A61M 11/042;
(Continued)

(56) References Cited

U.S. PATENT DOCUMENTS 5,012,804 A 5/1991 Foley et al.
5,040,527 A 8/1991 Larson et al.
(Continued)

FOREIGN PATENT DOCUMENTS

CN 1285759 A 2/2001
CN 1387447 A 12/2002
(Continued)

OTHER PUBLICATIONS

DE102018112711A1 Description Machine Translation accessed 20260321 (Year: 2026).*
(Continued)

*Primary Examiner* — Elliot S Ruddie
(74) *Attorney, Agent, or Firm* — Leydig, Voit & Mayer, Ltd.

(57) ABSTRACT

A vaporizer includes: a vapor generation device having a liquid storage cavity, a vaporization core, and a mounting portion, the liquid storage cavity storing an aerosol-generation substrate, and the vaporization core vaporizing the aerosol-generation substrate to generate vapor; and an air outlet channel insert to be inserted in the mounting portion, the air outlet channel insert including an outer wall, an inner wall, and a first air inlet channel, the inner wall encircling to form an air outlet channel, the outer wall being provided with a first airflow guide channel, and the first airflow guide channel being in communication with the first air inlet channel and the air outlet channel, respectively. When the air outlet channel insert is inserted in the mounting portion, the air outlet channel is in communication with the vaporization
(Continued)

core, and the first airflow guide channel is in communication with outside air.

20 Claims, 29 Drawing Sheets

(51) Int. Cl.
*A24F 40/10* (2020.01)
*A24F 40/48* (2020.01)
*A61M 11/04* (2006.01)
*A61M 15/00* (2006.01)
*A61M 15/06* (2006.01)

(52) U.S. Cl.
CPC ...... *A61M 11/042* (2014.02); *A61M 15/0021* (2014.02); *A61M 15/06* (2013.01)

(58) Field of Classification Search
CPC .............. A61M 15/0021; A61M 15/06; A61M 2206/20; A61M 11/00; A24D 3/18; B05B 17/00–085
See application file for complete search history.

(56) References Cited

U.S. PATENT DOCUMENTS

| | | | |
|---|---|---|---|
| 5,435,297 | A | 7/1995 | Klein |
| 10,098,381 | B2 | 10/2018 | Kane et al. |
| 10,292,424 | B2 | 5/2019 | Brammer et al. |
| 2011/0011395 | A1 | 1/2011 | Mazela et al. |
| 2013/0000641 | A1 | 1/2013 | Mazela et al. |
| 2014/0158123 | A1 | 6/2014 | Mazela et al. |
| 2014/0261492 | A1 | 9/2014 | Kane et al. |
| 2016/0198772 | A1 | 7/2016 | Thorens et al. |
| 2019/0150519 | A1 | 5/2019 | Liu et al. |
| 2019/0373949 | A1 | 12/2019 | Pan |
| 2019/0380387 | A1 | 12/2019 | Rose |

FOREIGN PATENT DOCUMENTS

| | | | | |
|---|---|---|---|---|
| CN | 1541125 | A | 10/2004 | |
| CN | 101980738 | A | 2/2011 | |
| CN | 103041480 | A | 4/2013 | |
| CN | 104736191 | A | 6/2015 | |
| CN | 204907913 | U | 12/2015 | |
| CN | 205456063 | U | 8/2016 | |
| CN | 205547375 | U | 9/2016 | |
| CN | 105982363 | A | 10/2016 | |
| CN | 205848684 | U | 1/2017 | |
| CN | 206525551 | U | 9/2017 | |
| CN | 107440161 | A | 12/2017 | |
| CN | 107581662 | A | 1/2018 | |
| CN | 208355880 | U | 1/2019 | |
| CN | 109718431 | A | 5/2019 | |
| CN | 110250579 | A | 9/2019 | |
| CN | 110558630 | A | 12/2019 | |
| CN | 110613171 | A | 12/2019 | |
| CN | 110623308 | A | 12/2019 | |
| CN | 111359060 | A | 7/2020 | |
| DE | 9204938 | U1 | 8/1993 | |
| DE | 102018112711 | A1 * | 11/2019 | ........ A61M 15/0085 |
| GB | 2279879 | A | 1/1995 | |
| WO | 0136033 | A2 | 5/2001 | |
| WO | 2004041338 | A1 | 5/2004 | |
| WO | 2014029827 | A1 | 2/2014 | |
| WO | 2015112750 | A1 | 7/2015 | |
| WO | 2017167512 | A1 | 10/2017 | |
| WO | 2018112755 | A1 | 6/2018 | |
| WO | 2018120206 | A1 | 7/2018 | |
| WO | WO-2019145159 | A1 * | 8/2019 | .......... A61M 15/009 |
| WO | 2019234055 | A1 | 12/2019 | |

OTHER PUBLICATIONS

Chinese Patent Office, Office Action in Chinese Patent Application No. 202010955466.2 (Feb. 28, 2023).
Chinese Patent Office, Office Action in Chinese Patent Application No. 202010859845.1 (Jan. 12, 2023).
Chinese Patent Office, Office Action in Chinese Patent Application No. 202010859124.0 (Jan. 20, 2023).
Chinese Patent Office, Third Office Action in Chinese Patent Application No. 202010859845.1 (Apr. 13, 2024).
Chinese Patent Office, Notification to Grant Patent Right for Invention in Chinese Patent Application No. 202010859845.1 (May 29, 2024).
Chinese Patent Office, Fourth Office Action in Chinese Patent Application No. 202010955466.2 (Apr. 11, 2024).
Chinese Patent Office, Notification to Grant Patent Right for Invention in Chinese Patent Application No. 202010955466.2 (May 29, 2024).
Chinese Patent Office, Office Action in Chinese Patent Application No. 202010955466.2 (Feb. 23, 2024).
Chinese Patent Office, Notification to Grant Patent Right for Invention in Chinese Patent Application No. 202010859124.0 (Jan. 2, 2024).
U.S. Patent and Trademark Office, Office Action in U.S. Appl. No. 17/820,801 (Nov. 10, 2025).
Patent Cooperation Treaty, International Search Report, International Application No. PCT/CN2020/110870 (Nov. 23, 2020).
Patent Cooperation Treaty, Written Opinion of the International Searching Authority, International Application No. PCT/CN2020/110870 (Nov. 23, 2020).
Chinese Patent Office, First Office Action in Chinese Patent Application No. 202010955466.2 (Aug. 3, 2022).
Patent Cooperation Treaty, International Search Report, International Application No. PCT/CN2021/072494 (Apr. 22, 2021).
Patent Cooperation Treaty, Written Opinion of the International Searching Authority, International Application No. PCT/CN2021/072494 (Apr. 22, 2021).
Patent Cooperation Treaty, International Search Report, International Application No. PCT/CN2020/110872 (Nov. 23, 2020).
Patent Cooperation Treaty, Written Opinion of the International Searching Authority, International Application No. PCT/CN2020/110872 (Nov. 23, 2020).
Patent Cooperation Treaty, International Search Report, International Application No. PCT/CN2020/114886 (Nov. 30, 2020).
Patent Cooperation Treaty, Written Opinion of the International Searching Authority, International Application No. PCT/CN2020/114886 (Nov. 30, 2020).
Chinese Patent Office, Rejection Decision in Chinese Patent Application No. 202010859845.1 (Sep. 5, 2023).
Chinese Patent Office, Rejection Decision in Chinese Patent Application No. 202010955466.2 (Jul. 21, 2023).
Chinese Patent Office, Office Action in Chinese Patent Application No. 202010859845.1 (Jul. 5, 2023).
Chinese Patent Office, Office Action in Chinese Patent Application No. 202010859124.0 (Aug. 7, 2023).
5 European Patent Office, Search Report in European Patent Application No. 20920396.7 (Aug. 3, 2023).

* cited by examiner (a)

(b)

(a)

(b)

ATOMIZER AND AIR OUTPUT CHANNEL PLUG-IN USED BY SAME, AND ELECTRONIC ATOMIZATION DEVICE

CROSS-REFERENCE TO PRIOR APPLICATION

This application is a continuation of International Patent Application No. PCT/CN2020/114886, filed on Sep. 11, 2020, which claims priority to Chinese Patent Application No. CN 202010105137.9, filed on Feb. 20, 2020, and PCT/CN2020/110870, filed on Aug. 24, 2020. The entire disclosure of both applications is hereby incorporated by reference herein.

FIELD

This application relates to the field of electronic vaporization device technologies, and in particular, to a vaporizer and an air outlet channel insert applicable thereto, and an electronic vaporization device.

BACKGROUND

Currently, air is introduced into an electronic vaporization device such as an e-cigarette mainly through an air inlet below a vaporizer, so that vapor is driven to be outputted to a user for inhalation by the user. Because in an existing vaporizer structure, e-liquid and vapor are mainly generated in close contact with an inner surface of the vaporizer, when the air enters from the air inlet below the vaporizer, the vapor is pushed by the air with a relatively high density toward an inner wall of the device from the center. Therefore, the vapor is always in close contact with the inner surface of the vaporizer during transmission of the vapor, and the air is always at a central position of an airway. Because the vapor generally has a relatively high temperature and the vapor is always in contact with the inner surface of the vaporizer, a large amount of heat in the vapor is lost due to heat exchange generated when the vapor is in contact with the inner surface of the vaporizer, leading to an increase of condensate inside the vaporizer or even liquid leakage.

SUMMARY

In an embodiment, the present invention provides a vaporizer, comprising: a vapor generation device comprising a liquid storage cavity, a vaporization core, and a mounting portion, the liquid storage cavity being configured to store an aerosol-generation substrate, and the vaporization core being configured to vaporize the aerosol-generation substrate to generate vapor; and an air outlet channel insert configured to be inserted in the mounting portion, the air outlet channel insert comprising an outer wall, an inner wall, and a first air inlet channel, the inner wall encircling to form an air outlet channel, the outer wall being provided with a first airflow guide channel, and the first airflow guide channel being in communication with the first air inlet channel and the air outlet channel, respectively, wherein, when the air outlet channel insert is inserted in the mounting portion, the air outlet channel is in communication with the vaporization core, and the first airflow guide channel is in communication with outside air to guide an external airflow to enter the air outlet channel through the first air inlet channel so as to form a blocking airflow between an inner wall of the air outlet channel insert and the vapor.

BRIEF DESCRIPTION OF THE DRAWINGS

Subject matter of the present disclosure will be described in even greater detail below based on the exemplary figures.

All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
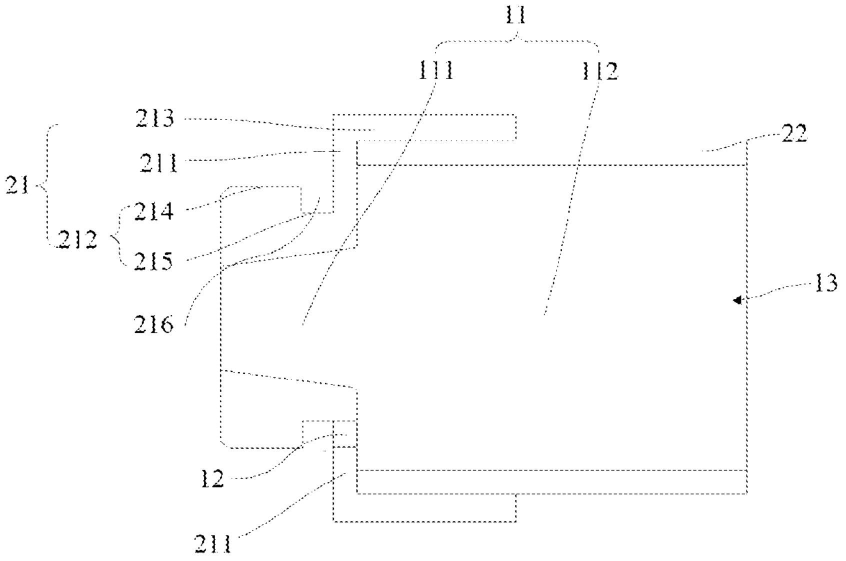
FIG. 1 is a schematic structural diagram of a first embodiment of a vaporization suction nozzle according to this application.

In an embodiment, the present invention provides provide a vaporizer and an air outlet channel insert applicable thereto, and an electronic vaporization device, to alleviate the problem of vapor condensation.

In an embodiment, the present invention provides a vaporizer. The vaporizer includes a vapor generation device. The vapor generation device includes a liquid storage cavity, a vaporization core, and a mounting portion, where the liquid storage cavity is configured to store an aerosol-generation substrate, and the vaporization core is configured to vaporize the aerosol-generation substrate to generate vapor. The vaporizer further includes an air outlet channel insert configured to be inserted in the mounting portion, where the air outlet channel insert includes an outer wall, an inner wall, and a first air inlet channel, the inner wall encircles to form an air outlet channel, the outer wall is provided with a first airflow guide channel, and the first airflow guide channel is in communication with the first air inlet channel and the air outlet channel respectively. When the air outlet channel insert is inserted in the mounting portion, the air outlet channel is in communication with the vaporization core, and the first airflow guide channel is in communication with the outside to guide an external airflow to enter the air outlet channel through the first air inlet channel, so as to form a blocking airflow between an inner wall of the air outlet channel insert and the vapor.

To resolve the technical problems, another technical solution adopted by this application is to provide an air outlet channel insert applicable to a vaporizer. The air outlet channel insert includes an air outlet channel. The air outlet channel is provided inside the air outlet channel insert and configured to convey vapor. The air outlet channel insert further includes a first air inlet channel. The first air inlet channel is provided on a side wall of the air outlet channel insert and in communication with the air outlet channel. The air outlet channel insert further includes a first airflow guide channel. The first airflow guide channel is provided on an outer wall of the air outlet channel insert, and the first airflow guide channel is in communication with the first air inlet channel and the outside to guide an external airflow to enter the air outlet channel through the first air inlet channel, so as to form a blocking airflow between an inner wall of the air outlet channel insert and the vapor.

To resolve the technical problems, another technical solution adopted by this application is to provide an electronic vaporization device. The electronic vaporization device includes an air outlet channel insert and a vapor generation device, and the air outlet channel insert is connected to the vapor generation device. The air outlet channel insert includes an air outlet channel. The air outlet channel is provided inside the air outlet channel insert and configured to convey vapor. The air outlet channel insert further includes a first air inlet channel. The first air inlet channel is provided on a side wall of the air outlet channel insert and in communication with the air outlet channel. The air outlet channel insert further includes a first airflow guide channel. The first airflow guide channel is provided on an outer wall of the air outlet channel insert, and the first airflow guide channel is in communication with the first air inlet channel and the outside to guide an external airflow to enter the air outlet channel through the first air inlet channel, so as to form a blocking airflow between an inner wall of the air outlet channel insert and the vapor.

Beneficial effects of this application are as follows: Different from the related art, this application provides a vaporizer and an air outlet channel insert applicable thereto, and an electronic vaporization device. An outer wall of the air outlet channel insert is provided with a first air inlet channel, and the first air inlet channel is configured to introduce an external airflow into an air outlet channel, to form a blocking airflow between an inner wall of the air outlet channel insert and vapor. In this application, the inner wall of the air outlet channel insert and the vapor are blocked by the blocking airflow, so that the vapor is in contact with the inner wall of the air outlet channel insert as little as possible. Therefore, the problem of vapor condensation can be alleviated, and formation of condensate can be reduced, thereby further reducing a risk of occurrence of liquid leakage and improving the use experience of a user.

In addition, the outer wall of the air outlet channel insert is further provided with a first airflow guide channel. The first airflow guide channel is in communication with the first air inlet channel and extends in a direction away from the first air inlet channel, and the first airflow guide channel is configured to guide an external airflow to enter the first air inlet channel, to ensure that the first air inlet channel has a sufficient air intake amount.

To make the objectives, technical solutions, and advantages of this application clearer, the following clearly and completely describes the technical solutions in the embodiments of this application with reference to the embodiments of this application. Apparently, the described embodiments are some rather than all of the embodiments of this application. All other embodiments obtained by a person of ordinary skill in the art based on the embodiments of this application without creative efforts shall fall within the protection scope of this application. The following embodiments and features in the embodiments may be mutually combined in a case that no conflict occurs.

To resolve the technical problem of relatively severe vapor condensation in the related art, an embodiment of this application provides a vaporization suction nozzle. The vaporization suction nozzle includes an air outlet channel. The air outlet channel is provided inside the vaporization suction nozzle and configured to convey vapor. The vaporization suction nozzle further includes a first air inlet channel. The first air inlet channel is provided on a side wall of the vaporization suction nozzle and in communication with the air outlet channel. The vaporization suction nozzle further includes a first airflow guide channel. The first airflow guide channel is provided on an outer wall of the vaporization suction nozzle, and the first airflow guide channel is in communication with the first air inlet channel and extends in a direction away from the first air inlet channel to guide an external airflow to enter the air outlet channel through the first air inlet channel, so as to form a blocking airflow between an inner wall of the vaporization suction nozzle and the vapor. Detailed descriptions are provided below.

Referring to FIG. 1, FIG. 1 is a schematic structural diagram of a first embodiment of a vaporization suction nozzle according to this application.

The following describes an exemplary embodiment in which an air-curtain forming structure is a vaporization suction nozzle applicable to an electronic vaporization device.

In this embodiment, the air-curtain forming structure is in the form of a vaporization suction nozzle. The vaporization suction nozzle provided in this embodiment may be applicable to electronic vaporization devices such as an e-cigarette and a medical vaporizer. Specifically, the vaporization suction nozzle includes an airflow channel 11, and the airflow channel 11 is configured to convey vapor. The vaporization suction nozzle further includes a first air inlet channel 12. The first air inlet channel 12 is in communication with the airflow channel 11, and the first air inlet channel 12 is configured to introduce an external airflow into the airflow channel 11, to form a blocking airflow between an inner wall of the airflow channel 11 and the vapor. The blocking airflow forms an air curtain.

Further, the vaporization suction nozzle further includes an air outlet 13 in communication with the airflow channel 11, the first air inlet channel 12 is close to the inner wall of the airflow channel 11, and an exit of the first air inlet channel 12 faces the air outlet 13, to ensure that the airflow entering the airflow channel 11 through the first air inlet channel 12 can flow along the inner wall of the airflow channel 11. That is, the blocking airflow is formed to block the vapor and the inner wall of the airflow channel 11, so that the vapor may be in contact with the inner wall of the airflow channel 11 as little as possible, thereby alleviating the problem of vapor condensation and reducing condensate formation.

Specifically, the vaporization suction nozzle includes an airway body 21 and a suction nozzle portion. The suction nozzle portion includes a tube body 22, and the airflow channel 11 is provided in the airway body 21 and the tube body 22. One end of the tube body 22 away from the airway body 21 is the air outlet 13. The first air inlet channel 12 is provided at a position of the airway body 21 close to an inner wall of the tube body 22, to form a blocking airflow between the inner wall of the tube body 22 and the vapor.

The airflow channel 11 includes an entrance channel 111 and an air guide channel 112. The tube body 22 includes the air guide channel 112. The airway body 21 is mounted at one end of the tube body 22, the airway body 21 includes the entrance channel 111, and the entrance channel 111 of the airway body 21 is in communication with the air guide channel 112 of the tube body 22. The entrance channel 111 is configured to introduce the vapor and convey the vapor into the air guide channel 112.

Figure 2:
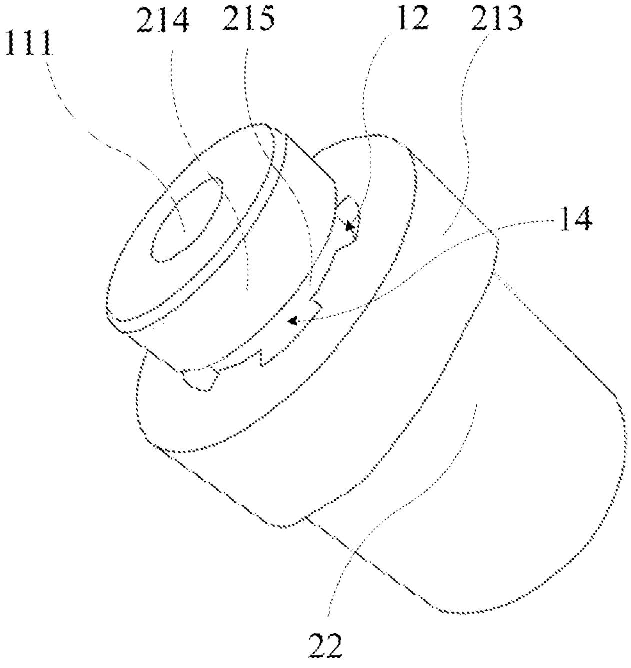
FIG. 2 is a three-dimensional schematic structural diagram of a first embodiment of a vaporization suction nozzle according to this application.

Referring to FIG. 1 and FIG. 2, FIG. 2 is a three-dimensional schematic structural diagram of a first embodiment of a vaporization suction nozzle according to this application. When the airway body 21 is mounted at one end of the tube body 22, a part of the airway body abuts against one end of the air guide channel 112 and covers a part of the air guide channel 112. The first air inlet channel 12 in communication with the air guide channel 112 is provided at a position where the airway body 21 covers the air guide channel 112. Optionally, the airway body 21 includes a wall portion 211 abutting against one end of the air guide channel 112 and covering a part of the air guide channel 112, and the first air inlet channel 12 is provided on the wall portion 211 and is in communication with the air guide channel 112.

Condensate is easily formed on an inner wall of the air guide channel 112 due to moisture in the vapor. The first air inlet channel 12 is provided, and air is introduced into the first air inlet channel 12. When inhalation is performed at the vaporization suction nozzle, that is, inhalation is performed from the end of the tube body 22 away from the airway body 21, an air pressure difference is formed inside the vaporization suction nozzle, so that under the action of the air pressure difference, air entering through the first air inlet channel 12 is adhered to the inner wall of the air guide channel 112 and forms a blocking airflow on the inner wall of the air guide channel 112, to block the vapor and the inner wall of the air guide channel 112, thereby reducing condensate formed by the vapor on the inner wall of the air guide channel 112. When no inhalation is performed at the vaporization suction nozzle, there is no air pressure difference inside the vaporization suction nozzle, and there is no blocking airflow formed on the inner wall of the air guide channel 112.

Further, a flow direction of the blocking airflow is parallel to the inner wall of the airflow channel 11. That is, the flow direction of the blocking airflow is parallel to the inner wall of the air guide channel 112. To be specific, the flow direction of the blocking airflow is parallel to the inner wall of the tube body 22, to ensure a favorable effect of the blocking airflow for blocking the vapor and the inner wall of the tube body 22.

Optionally, to cause the blocking airflow to be adhered to the inner wall of the air guide channel 112 to form an air curtain, in a specific embodiment, there may be a plurality of first air inlet channels 12, and the plurality of first air inlet channels 12 are arranged at intervals in a circumferential direction of the wall portion 211.

Figure 3:
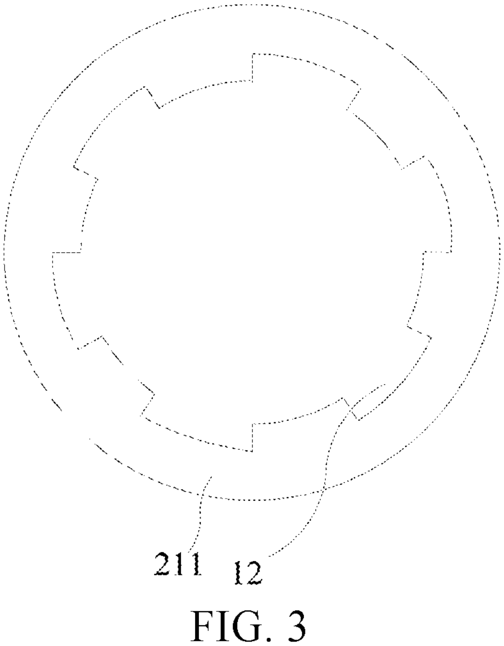
FIG. 3 is a schematic structural diagram of a first air inlet channel of an airway body of a vaporization suction nozzle according to this application.

Referring to FIG. 3, FIG. 3 is a schematic structural diagram of a first air inlet channel of an airway body of a vaporization suction nozzle according to this application. The airway body 21 includes a wall portion 211 covering the air guide channel 112. The first air inlet channel 12 is provided on the wall portion 211 and is in communication with the air guide channel 112. As shown in FIG. 3, there are a plurality of first air inlet channels 12 uniformly arranged in the circumferential direction of the wall portion 211. In a specific embodiment, a shape of the first air inlet channel 12 is not limited, provided that air can enter the air guide channel 112 through the first air inlet channel during inhalation. In an optional embodiment, the shape of the first air inlet channel 12 may be any one of or any combination of a square, a circle, or a triangle.

Further, when the size of the first air inlet channel 12 is appropriately planned during arrangement of the first air inlet channel, air entering through the first air inlet channel 12 can form a blocking airflow completely covering the inner wall of the air guide channel 112 on the inner wall of the air guide channel 112.

Still referring to FIG. 1, the airway body 21 of the vaporization suction nozzle in this application includes a first airway portion 212, a second airway portion 213, and the wall portion 211 connecting the first airway portion 212 and the second airway portion 213 and covering a part of the air guide channel 112. The entrance channel 111 is mainly provided in the first airway portion 212 and is in communication with the air guide channel 112, and the second airway portion 213 is sleeved on an outer side of the tube body 22 of the suction nozzle portion. In a specific embodiment, the wall portion 211 abuts against one end of the air guide channel 112. In another embodiment, there may be a gap between the wall portion 211 and one end of the air guide channel 112, provided that vapor leakage does not occur.

Optionally, still referring to FIG. 2, the first airway portion 212 further includes a vent portion 214 and a first connection portion 215, where the first connection portion 215 is arranged on one side of the wall portion 211 away from the second airway portion 213, and the vent portion 214 is arranged on one side of the first connection portion 215 away from the wall portion 211. A cross-sectional area (where the cross-section is defined as a section perpendicular to an axial direction, which is the same below) of the first connection portion 215 is less than a cross-sectional area of the vent portion 214. A clamping opening 216 is formed at a position where the first connection portion 215 is connected to the vent portion 214, and the clamping opening 216 is configured to clamp a vapor generation device (that is, a part of the electronic vaporization device for generating vapor). Further, referring to FIG. 1 and FIG. 2, a comprehensive airway 14 is formed at a position of the clamping opening 216, so that air enters the first air inlet channel 12 through the comprehensive airway 14 and then enters the air guide channel 112 through the first air inlet channel 12. During inhalation, after an air pressure difference is generated, a blocking airflow is formed on the inner wall of the air guide channel 112 under the action of the air pressure difference. The blocking airflow blocks the vapor and the air guide channel 112, thereby reducing condensate formed by the vapor in the air guide channel 112.

Optionally, in an implementation, the first airway portion 212, the second airway portion 213, and the wall portion 211 connecting the first airway portion 212 and the second airway portion 213 of the airway body 21 are integrally formed. In another implementation, the first airway portion 212, the second airway portion 213, and the wall portion 211 connecting the first airway portion 212 and the second airway portion 213 of the airway body 21 may also be formed by connection through a process such as welding.

Optionally, the second airway portion 213 of the airway body 21 is sleeved on the outer side of the tube body 22 of the suction nozzle portion. Specifically, in an implementation, the airway body 21 and the tube body 22 may be designed to be integrally formed. In another implementation, the second airway portion 213 may alternatively be sleeved on the outer side of the tube body 22 of the suction nozzle portion in a matching manner. To avoid vapor leakage, the second airway portion may be sleeved on the outer side of the tube body 22 of the suction nozzle portion in an interference-fitting manner.

According to the vaporization suction nozzle provided in this embodiment, the first air inlet channel 12 in communication with the air guide channel 112 is provided on the wall portion 211 covering the air guide channel 112. When an inhalation action is performed on the tube body 22, while the vapor enters the air guide channel 112 through the entrance channel 111, air enters the air guide channel through the first air inlet channel 12. The air entering through the first air inlet channel 12 forms a blocking airflow on the inner wall of the air guide channel 112 under the action of an air pressure, to block the vapor and the inner wall of the air guide channel 112, thereby preventing the vapor from forming condensate on the inner wall of the air guide channel 112.

Figure 4:
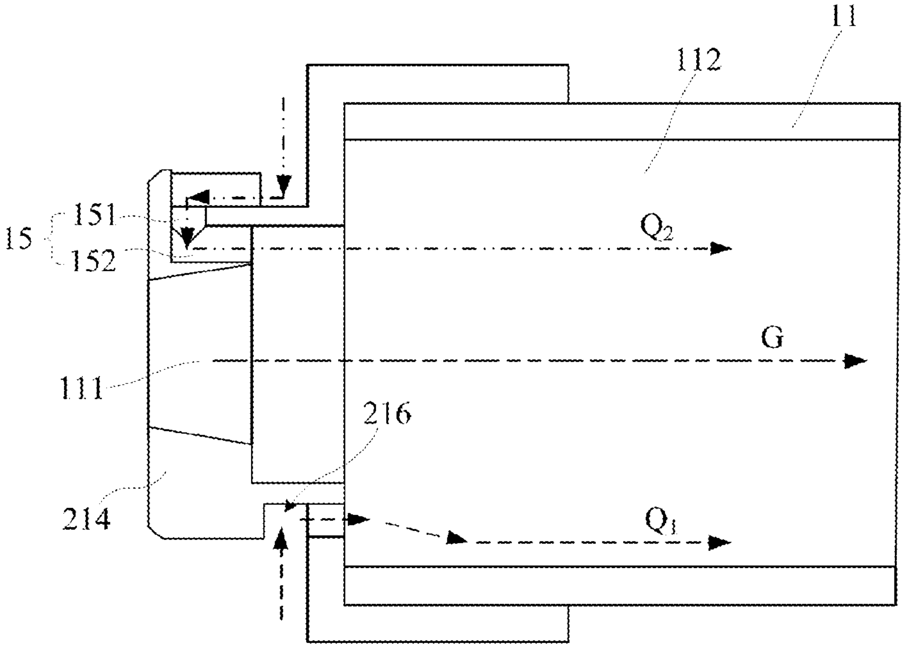
FIG. 4 is a schematic structural diagram of a second embodiment of a vaporization suction nozzle according to this application.

Referring to FIG. 4, FIG. 4 is a schematic structural diagram of a second embodiment of a vaporization suction nozzle according to this application. Compared with the first embodiment shown in FIG. 1, a difference between the first embodiment and the second embodiment is that: in this embodiment, a second air inlet channel 15 is provided on an outer side of the vent portion 214. The second air inlet channel 15 is configured to increase a discharge speed of the vapor, to further prevent the vapor from forming condensate on the inner wall of the air guide channel 112.

Optionally, the second air inlet channel 15 includes an air inlet portion 151 and an air guide portion 152. Specifically, the air inlet portion 151 is arranged surrounding the vent portion in a direction parallel to the wall portion 211, an extending direction of the air guide portion 152 is arranged parallel to an extending direction of the entrance channel 111, and the air guide portion 152 is connected to one end of the air inlet portion 151 that is arranged in the vent portion 214. Air enters through the air inlet portion 151 and flows to the air guide channel 112 through the air guide portion 152.

Figure 5:
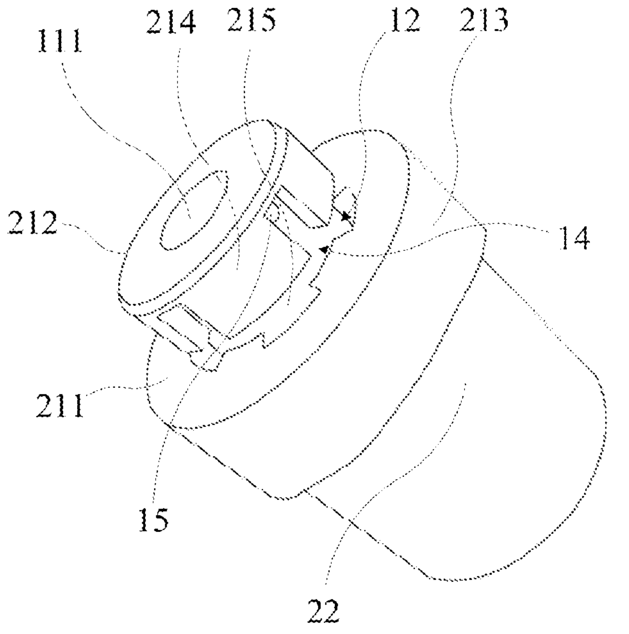
FIG. 5 is a three-dimensional schematic structural diagram of a second embodiment of a vaporization suction nozzle according to this application.
Figure 6:
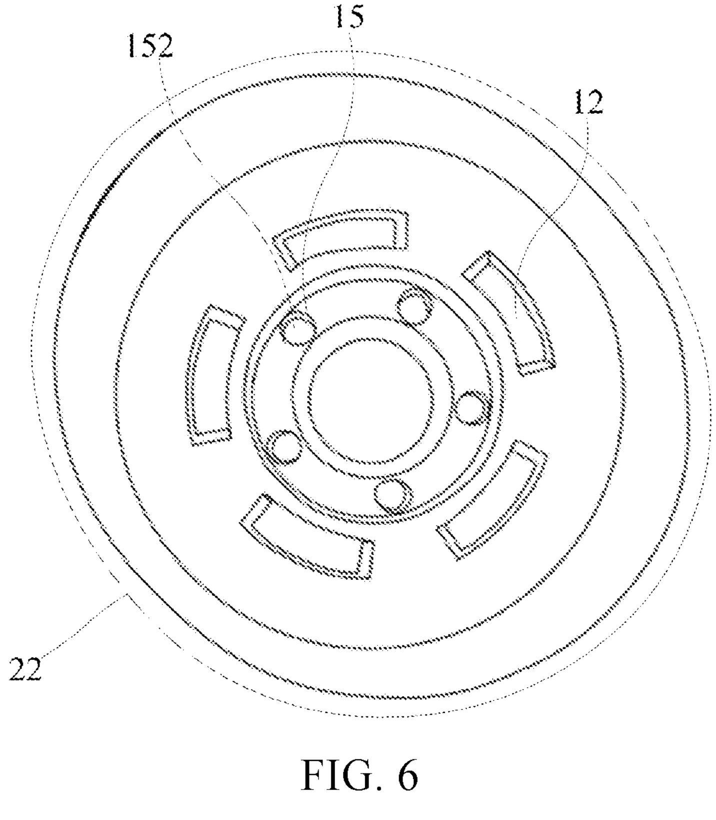
FIG. 6 is a schematic bottom structural view of a second embodiment of a vaporization suction nozzle according to this application.

Optionally, referring to FIG. 4 and FIG. 5, FIG. 5 is a three-dimensional schematic structural diagram of a second embodiment of a vaporization suction nozzle according to this application. The second air inlet channel 15 is provided in the vent portion 214, and the first air inlet channel 12 is provided on the wall portion 211 connecting the first airway portion 212 and the second airway portion 213. In a specific embodiment, when the tube body 22 of the suction nozzle portion generates an inhalation force, the vapor enters through the entrance channel 111, and air enters through the second air inlet channel 15 and the first air inlet channel 12. Referring to FIG. 6, FIG. 6 is a schematic bottom structural view of a second embodiment of a vaporization suction nozzle according to this application. As shown in FIG. 6, the first air inlet channel 12 is closer to the inner wall of the tube body 22 relative to the air guide portion 152 in the second air inlet channel 15. Therefore, during inhalation, under the action of an air pressure, air entering through the first air inlet channel 12 forms a blocking airflow on the inner wall of the air guide channel of the tube body 22 of the suction nozzle portion, to block the vapor entering through the entrance channel 111 and the inner wall of the air guide channel, and reduce condensate formed by the vapor on the inner wall of the air guide channel. Further, the second air inlet channel 15 is provided, air enters the second air inlet channel 15 during inhalation, and the air increases the discharge speed of the vapor entering through the entrance channel 111 in the air guide channel 112, thereby further preventing the vapor from forming condensate on the inner wall of the air guide channel.

Further, still referring to FIG. 4 and FIG. 5, a clamping opening 216 is formed at a position where the first connection portion 215 is connected to the vent portion 214, and the clamping opening 216 is configured to clamp a vapor generation device. Further, a comprehensive airway 14 is formed at a position of the clamping opening 216, so that air enters the first air inlet channel 12 and the second air inlet channel 15 through the comprehensive airway 14 and then enters the air guide channel 112 through the first air inlet channel 12. During inhalation, after an air pressure difference is generated, a blocking airflow is formed on the inner wall of the air guide channel 112 under the action of the air pressure difference. As shown in FIG. 4, the blocking airflow (as shown by an arrow Q1 in FIG. 4) blocks the vapor (as shown by an arrow G in FIG. 4) and the air guide channel 112, thereby reducing condensate formed by the vapor on the inner wall of the air guide channel 112. Air enters the air guide portion 152 through the second air inlet channel 15 and forms a second airflow while entering the air guide channel 112. The second airflow increases the discharge speed of the vapor.

Optionally, in this embodiment, a shape of the air guide portion 152 of the second air inlet channel 15 may be any one of or any combination of a square, a circle, or a triangle. A shape of the air inlet portion 151 of the second air inlet channel 15 may also be any one of or any combination of a square, a circle, or a triangle, which is not specifically limited provided that air can be introduced into the air guide portion 152 and then enter the air guide channel 112.

In an embodiment, there is at least one second air inlet channel 15 circumferentially provided on an outer side of the vent portion 214.

In an embodiment, the second air inlet channels 15 may be provided corresponding to the first air inlet channels 12. In another embodiment, the second air inlet channels 15 and the first air inlet channels 12 may alternatively be staggered. Specifically, to reduce the mutual impact between airflows formed by air entering the first air inlet channels 12 and the second air inlet channels 15, as shown in FIG. 6, the second air inlet channels 15 and the first air inlet channels 12 are staggered.

In an embodiment, when the first air inlet channels 12 and the second air inlet channels 15 are provided, there is a speed difference between the airflows formed in the second air inlet channels 15 and the first air inlet channels 12, to ensure that air entering through the first air inlet channels 12 forms a blocking airflow on the inner wall of the air guide channel 112, which can block the vapor and the air guide channel 112, and air entering through the second air inlet channels 15 can increase the discharge speed of the vapor. In a specific embodiment, a flow rate of the airflows formed in the first air inlet channels 12 is greater than a flow rate of the airflows formed in the second air inlet channels 15, thereby weakening the impact on a convey direction of the vapor while achieving the effect of reducing condensate.

Specifically, the flow rates of the airflows formed in the first air inlet channel 12 and the second air inlet channel 15 are related to a size of an opening. That is, a greater size of the opening indicates a faster flow rate. Therefore, in a specific implementation, to realize that the flow rate of the airflow formed in the first air inlet channel 12 is greater than the flow rate of the airflow formed in the second air inlet channel 15, a size of the first air inlet channel 12 (that is, a cross-sectional area, where a cross-section of the first air inlet channel 12 should be a section taken in a direction perpendicular to an extending direction of the first air inlet channel 12) is set to be greater than a size of the second air inlet channel 15 (that is, a cross-sectional area, where a cross-section of the second air inlet channel 15 should be a section taken in a direction perpendicular to an extending direction of the second air inlet channel 15). Alternatively, in another embodiment, a number of the first air inlet channels 12 is greater than a number of the second air inlet channels 15.

As shown in FIG. 4, when an air pressure difference is generated due to inhalation by a user, under the action of the air pressure difference, an external airflow enters the airflow channel 11 (that is, the air guide channel 112) through the first air inlet channel 12 and then forms a blocking airflow Q1 on the inner wall of the airflow channel 11. The blocking airflow Q1 blocks the vapor G and the inner wall of the airflow channel 11, to reduce condensate formed by the vapor G on the inner wall of the airflow channel 11. In addition, under the action of the air pressure difference, an airflow Q2 entering the airflow channel 11 through the second air inlet channel 15 flows along an outer edge of the vapor G, to increase the discharge speed of the vapor G.

Figure 7:
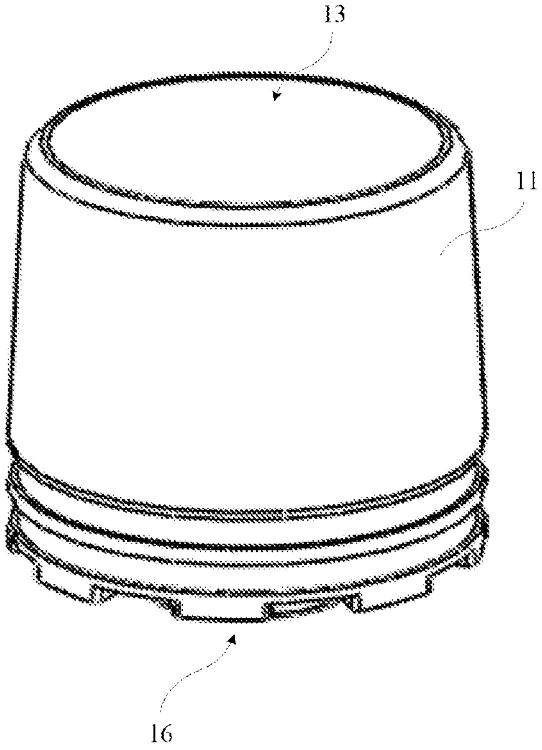
FIG. 7 is a schematic structural diagram of a third embodiment of a vaporization suction nozzle according to this application.
Figure 8:
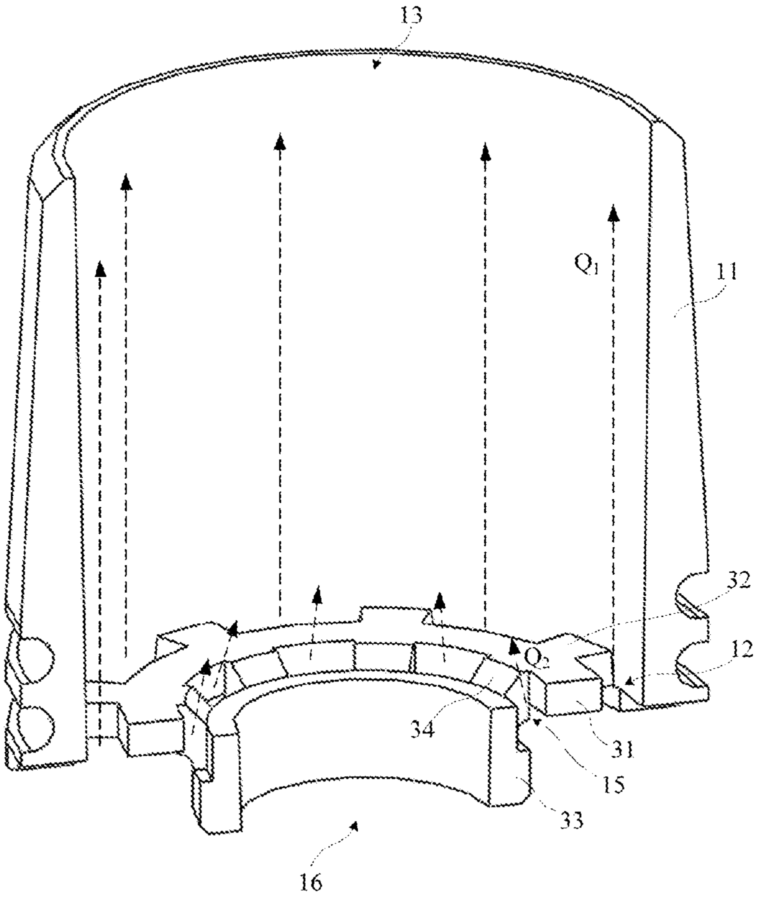
FIG. 8 is a schematic cross-sectional structural view of a third embodiment of a vaporization suction nozzle according to this application.

Referring to FIG. 7 and FIG. 8, FIG. 7 is a schematic structural diagram of a third embodiment of a vaporization suction nozzle according to this application, and FIG. 8 is a schematic cross-sectional structural view of a third embodiment of a vaporization suction nozzle according to this application.

The following describes an exemplary embodiment in which an air-curtain forming structure is a vaporization suction nozzle applicable to an electronic vaporization device.

in this embodiment, the air-curtain forming structure is in the form of a vaporization suction nozzle. The vaporization suction nozzle provided in this embodiment may be applicable to electronic vaporization devices such as an e-cigarette and a medical vaporization electronic device.

Specifically, the vaporization suction nozzle includes an airflow channel 11, and the airflow channel 11 is configured to convey vapor. The vaporization suction nozzle further includes a first air inlet channel 12. The first air inlet channel 12 is in communication with the airflow channel 11, and the first air inlet channel 12 is configured to introduce an external airflow into the airflow channel 11, to form a blocking airflow (as shown by an arrow Q1 in FIG. 8, which is the same below) between an inner wall of the airflow channel 11 and the vapor. The blocking airflow forms an air curtain.

Further, the vaporization suction nozzle is further provided with a first air inlet 16 and an air outlet 13. The first air inlet 16 and the air outlet 13 are provided opposite to each other and in communication with the airflow channel 11 respectively. Vapor enters the airflow channel 11 through the first air inlet 16 and is conveyed to the air outlet 13 through the airflow channel 11, and then the vapor is outputted from the air outlet 13 for a user to inhale. The first air inlet channel 12 is close to the inner wall of the airflow channel 11, and an exit of the first air inlet channel 12 faces the air outlet 13, to ensure that the airflow entering the airflow channel 11 through the first air inlet channel 12 can flow along the inner wall of the airflow channel 11 (that is, the inner wall of the vaporization suction nozzle). That is, the blocking airflow (as shown by the arrow Q1 in FIG. 8, which is the same below) is formed to block the vapor and the inner wall of the airflow channel 11, namely, to block the vapor and the inner wall of the vaporization suction nozzle, so that the vapor may be in contact with the inner wall of the vaporization suction nozzle as little as possible, thereby alleviating the problem of vapor condensation and reducing condensate formation.

Further, a flow direction of the blocking airflow is parallel to the inner wall of the airflow channel 11. That is, the flow direction of the blocking airflow is parallel to the inner wall of the vaporization suction nozzle, to ensure a favorable effect of the blocking airflow for blocking the vapor and the inner wall of the vaporization suction nozzle.

In an embodiment, still referring to FIG. 8, the vaporization suction nozzle further includes a first airflow guide portion 31. The first air inlet channel 12 is formed between the first airflow guide portion 31 and the inner wall of the airflow channel 11, and the first airflow guide portion is configured to guide an airflow introduced through the first air inlet channel 12 to flow along the inner wall of the airflow channel 11, to form the blocking airflow.

Further, the vaporization suction nozzle further includes a second connection portion 32. The first airflow guide portion 31 is connected to the inner wall of the airflow channel 11 through the second connection portion 32.

Figure 9:
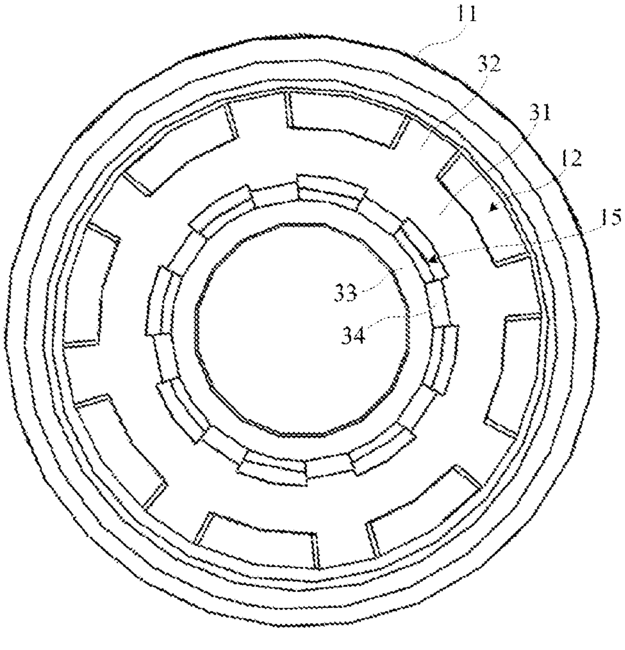
FIG. 9 is a schematic top structural view of a third embodiment of a vaporization suction nozzle according to this application.

Specifically, referring to FIG. 9, a plurality of second connection portions 32 are arranged between the first airflow guide portion 31 and the inner wall of the airflow channel 11. The plurality of second connection portions 32 are arranged at intervals sequentially in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channel 12 between the first airflow guide portion 31 and the inner wall of the airflow channel 11 is also ensured.

Further, a plurality of first air inlet channels 12 may be formed between the first airflow guide portion 31 and the inner wall of the airflow channel 11, and as shown in FIG. 8, blocking airflows formed by the plurality of first air inlet channels 12 form an air curtain, which greatly causes the vapor to be in contact with the inner wall of the vaporization suction nozzle (that is, the inner wall of the airflow channel 11) as little as possible. Therefore, the problem of vapor condensation can be alleviated, and condensate formation can be reduced.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 8, the vaporization suction nozzle further includes a second airflow guide portion 33. The second airflow guide portion 33 is away from the inner wall of the airflow channel 11 relative to the first airflow guide portion 31, a second air inlet channel 15 is formed between the second airflow guide portion 33 and the first airflow guide portion 31, an exit of the second air inlet channel 15 faces the air outlet 13, and an airflow (as shown by an arrow Q2 in FIG. 8) entering through the second air inlet channel 15 is used to guide the vapor to be outputted from the air outlet 13, thereby speeding up discharging of the vapor.

Further, the second airflow guide portion 33 is annularly arranged to encircle to form the first air inlet 16 of the vaporization suction nozzle.

Further, the air-curtain forming structure further includes a third connection portion 34, and the second airflow guide portion 33 is connected to the first airflow guide portion 31 through the third connection portion 34, so that a relative position of the second airflow guide portion 33 in the vaporization suction nozzle is fixed through the first airflow guide portion 31.

Specifically, referring to FIG. 9, a plurality of third connection portions 34 are arranged between the second airflow guide portion 33 and the first airflow guide portion 31, the plurality of third connection portions 34 are arranged at intervals sequentially in a circumferential direction of the second airflow guide portion 33, and the second air inlet channel 15 is formed between adjacent third connection portions 34. In this way, the relative position of the second airflow guide portion 33 in the vaporization suction nozzle is fixed, and formation of the second air inlet channel 15 between the second airflow guide portion 33 and the first airflow guide portion 31 is ensured.

Figure 10:
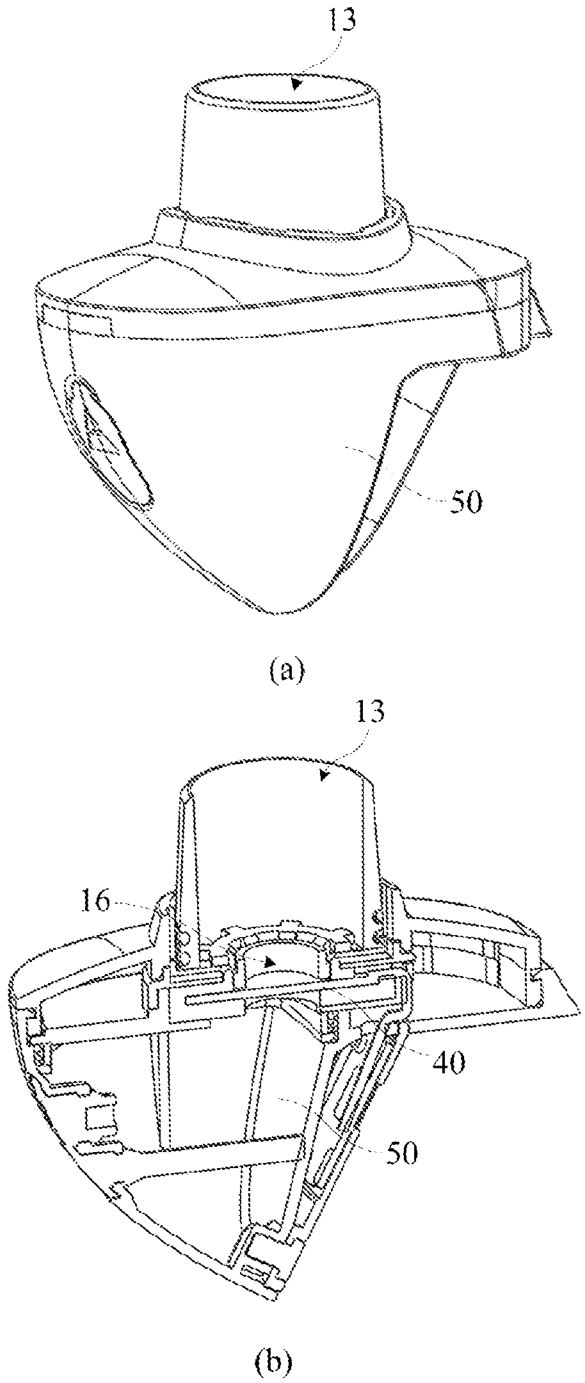
FIG. 10 is a schematic structural diagram of a first embodiment of a vaporizer according to this application.
Figure 11:
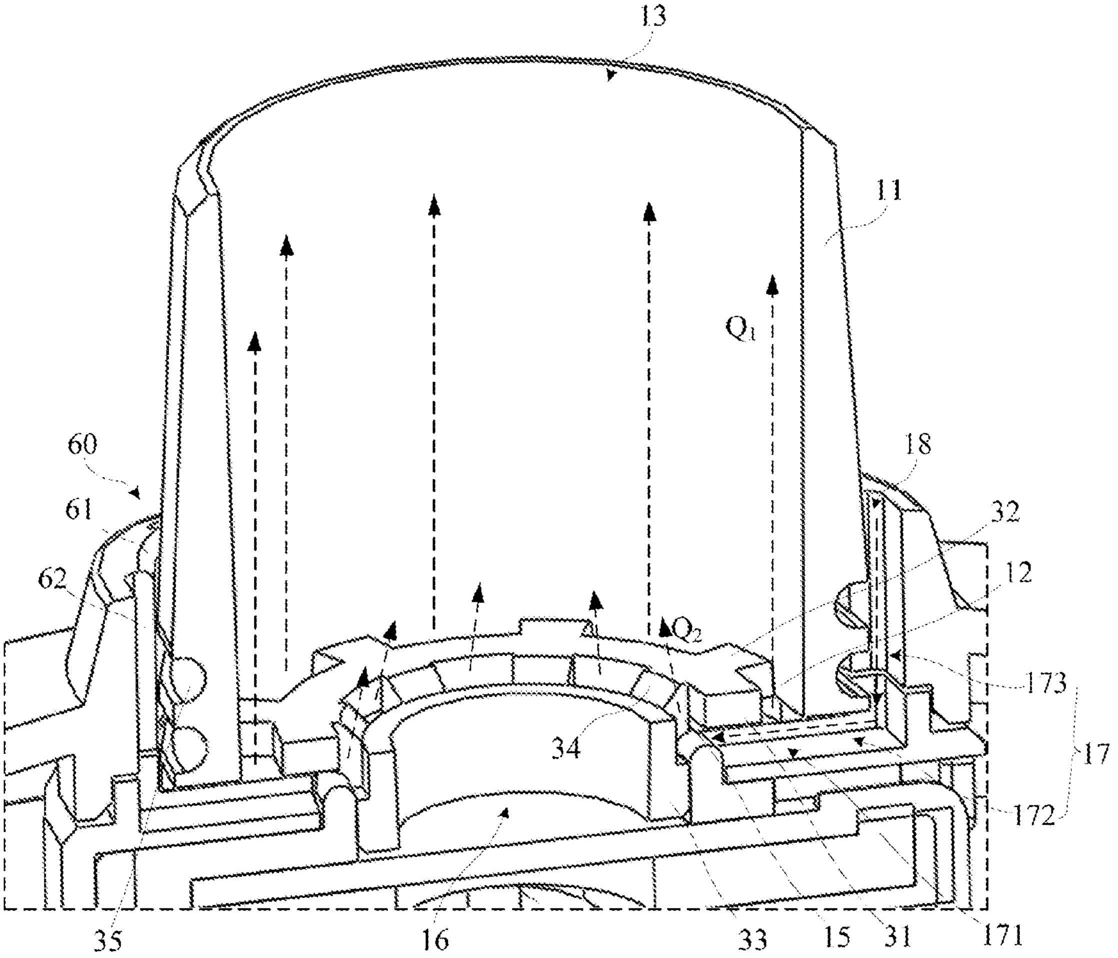
FIG. 11 is a schematic partial cross-sectional structural view of a first embodiment of a vaporizer according to this application.

Referring to FIG. 10 and FIG. 11, FIG. 10 is a schematic structural diagram of a first embodiment of a vaporizer according to this application, and FIG. 11 is a schematic partial cross-sectional structural view of a first embodiment of a vaporizer according to this application.

The following describes an exemplary embodiment in which an air-curtain forming structure is a vaporizer applicable to an electronic vaporization device.

In this embodiment, the air-curtain forming structure is in the form of a vaporizer. The vaporizer provided in this embodiment may be applicable to electronic vaporization devices such as an e-cigarette and a medical vaporizer. FIG. 10 shows a situation in which the air-curtain forming structure is applicable to a medical vaporizer, which is merely used for description and is not intended to constitute a limitation to an application environment of the air-curtain forming structure in this embodiment.

In this embodiment, referring to FIG. 10, the air-curtain forming structure includes a vaporization suction nozzle, a vaporization core 40, and a liquid storage cavity 50. The vaporization suction nozzle is provided with a first air inlet 16 and an air outlet 13, vapor enters the vaporization suction nozzle through the first air inlet 16 and is conveyed to the air outlet 13 through the vaporization suction nozzle, and then the vapor is outputted from the air outlet 13 for a user to inhale. The vaporization core 40 is arranged at a position of the first air inlet 16 of the vaporization suction nozzle and is configured to vaporize an aerosol-generation substrate stored in the liquid storage cavity 50 to generate vapor. A vapor generation device of the air-curtain forming structure in this embodiment includes structures such as the vaporization core 40 and the liquid storage cavity 50, and is configured to generate vapor.

For the situation in which the air-curtain forming structure in this embodiment is applicable to a medical vaporizer, the vaporization core 40 may be an ultrasonic vaporization sheet, and the ultrasonic vaporization sheet vaporizes the aerosol-generation substrate through high-frequency oscillation to generate vapor. The specific principle thereof falls within the scope understood by a person skilled in the art, and details are not described herein again. Certainly, for situations in which the air-curtain forming structure is applicable to other fields, the vaporization core 40 may also heat and vaporize the aerosol-generation substrate to generate vapor, which is not limited herein.

Specifically, referring to FIG. 11, the vaporization suction nozzle includes an airflow channel 11, and the airflow channel 11 is configured to convey vapor. The vaporization suction nozzle further includes a first air inlet channel 12. The first air inlet channel 12 is in communication with the airflow channel 11, and the first air inlet channel 12 is configured to introduce an external airflow into the airflow channel 11, to form a blocking airflow (as shown by an arrow Q1 in FIG. 11, which is the same below) between an inner wall of the airflow channel 11 and the vapor. The blocking airflow forms an air curtain.

Further, the first air inlet 16 and the air outlet 13 are provided opposite to each other and are in communication with the airflow channel 11 respectively. The first air inlet channel 12 is close to the inner wall of the airflow channel 11, and an exit of the first air inlet channel 12 faces the air outlet 13, to ensure that the airflow entering the airflow channel 11 through the first air inlet channel 12 can flow along the inner wall of the airflow channel 11 (that is, the inner wall of the vaporization suction nozzle). That is, the blocking airflow is formed to block the vapor and the inner wall of the airflow channel 11, namely, to block the vapor and the inner wall of the vaporization suction nozzle, so that the vapor may be in contact with the inner wall of the vaporization suction nozzle as little as possible, thereby alleviating the problem of vapor condensation and reducing condensate formation.

Further, a flow direction of the blocking airflow is parallel to the inner wall of the airflow channel 11. That is, the flow direction of the blocking airflow is parallel to the inner wall of the vaporization suction nozzle, to ensure a favorable effect of the blocking airflow for blocking the vapor and the inner wall of the vaporization suction nozzle.

In an embodiment, still referring to FIG. 11, the vaporization suction nozzle further includes a first airflow guide portion 31. The first air inlet channel 12 is formed between the first airflow guide portion 31 and the inner wall of the airflow channel 11, and the first airflow guide portion is configured to guide an airflow introduced through the first air inlet channel 12 to flow along the inner wall of the airflow channel 11, to form the blocking airflow.

Further, the vaporization suction nozzle further includes a second connection portion 32. The first airflow guide portion 31 is connected to the inner wall of the airflow channel 11 through the second connection portion 32.

Specifically, a plurality of second connection portions 32 are arranged between the first airflow guide portion 31 and the inner wall of the airflow channel 11. The plurality of second connection portions 32 are arranged at intervals sequentially in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channel 12 between the first airflow guide portion 31 and the inner wall of the airflow channel 11 is also ensured.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 11, the vaporization suction nozzle further includes a second airflow guide portion 33. The second airflow guide portion 33 is away from the inner wall of the airflow channel 11 relative to the first airflow guide portion 31, a second air inlet channel 15 is formed between the second airflow guide portion 33 and the first airflow guide portion 31, an exit of the second air inlet channel 15 faces the air outlet 13, and an airflow entering through the second air inlet channel 15 is used to guide the vapor to be outputted from the air outlet 13, thereby speeding up discharging of the vapor.

Further, the second airflow guide portion 33 is annularly arranged to encircle to form the first air inlet 16 of the vaporization suction nozzle.

Further, the air-curtain forming structure further includes a third connection portion 34, and the second airflow guide portion 33 is connected to the first airflow guide portion 31 through the third connection portion 34, so that a relative position of the second airflow guide portion 33 in the vaporization suction nozzle is fixed through the first airflow guide portion 31.

Specifically, a plurality of third connection portions 34 are arranged between the second airflow guide portion 33 and the first airflow guide portion 31, the plurality of third connection portions 34 are arranged at intervals sequentially in a circumferential direction of the second airflow guide portion 33, and the second air inlet channel 15 is formed between adjacent third connection portions 34. In this way, the relative position of the second airflow guide portion 33 in the vaporization suction nozzle is fixed, and formation of the second air inlet channel 15 between the second airflow guide portion 33 and the first airflow guide portion 31 is ensured.

In an embodiment, still referring to FIG. 11, the air-curtain forming structure further includes a converging channel 17, one end of the converging channel 17 is an air inlet, that is, a second air inlet 18, and the other end of the converging channel is a diverging opening 171, where the diverging opening 171 is in communication with the first air inlet channel 12 and the second air inlet channel 15 respectively.

Specifically, the converging channel 17 includes a first channel section 172 and a second channel section 173 that are in communication with each other, an end opening of the first channel section 172 away from the second channel section 173 is the diverging opening 171, and an end opening of the second channel section 173 away from the first channel section 172 is the air inlet, that is, the second air inlet 18. An extending direction of the first channel section 172 is different from an extending direction of the second channel section 173.

FIG. 11 shows that the extending direction of the first channel section 172 is a horizontal direction, the extending direction of the second channel section 173 is a vertical direction, and the second channel section 173 extends toward the air outlet 13. When the user performs inhalation, an external airflow enters the second channel section 173 through the second air inlet 18 and is conveyed to the first channel section 172, and then the airflow passes through the diverging opening 171 and enters the airflow channel 11 in the vaporization suction nozzle through the first air inlet channel 12 and the second air inlet channel 15 respectively, where flow conditions of airflows are shown by dashed-line arrows in FIG. 11.

Further, the air-curtain forming structure is provided with a mounting portion 60. The mounting portion 60 is provided with a mounting protrusion 61 and a vent groove 62, where the mounting protrusion 61 is configured to fix the vaporization suction nozzle. After the vaporization suction nozzle is fixed to the mounting portion 60, the first channel section 172 is formed between the vaporization suction nozzle and the mounting portion 60, and to be specific, the first channel section 172 is formed between the vaporization suction nozzle and a bottom portion of the mounting portion 60. In addition, the second channel section 173 is formed between the vent groove 62 and the vaporization suction nozzle.

In an embodiment, still referring to FIG. 11, a periphery of the vaporization suction nozzle is provided with a limiting groove 35 surrounding in a circumferential direction of the vaporization suction nozzle, where the limiting groove 35 is configured to place an elastic ring to fix the vaporization suction nozzle. Specifically, after the vaporization suction nozzle is embedded in the mounting portion 60 described above, the elastic ring placed in the limiting groove 35 is in elastically interference fit with the mounting protrusion 61 in the mounting portion 60, to fix the vaporization suction nozzle in the mounting portion 60.

It should be noted that, the elastic ring arranged at a position of the vent groove 62 in the mounting portion 60 does not block a gap between the vaporization suction nozzle and the vent groove 62, to ensure a ventilation function between the vaporization suction nozzle and the vent groove 62, thereby ensuring that the external airflow can enter the airflow channel 11 to form a blocking airflow and speed up discharging of the vapor.

Optionally, there may be a plurality of limiting grooves 35, and the plurality of limiting grooves 35 are provided at intervals in an axial direction of the vaporization suction nozzle. By designing a plurality of limiting grooves 35, sufficient bonding strength between the vaporization suction nozzle and the mounting portion 60 can be ensured, to prevent the vaporization suction nozzle from falling off. In addition, the elastic ring may be a silicone ring, which is not limited herein.

Figure 12:
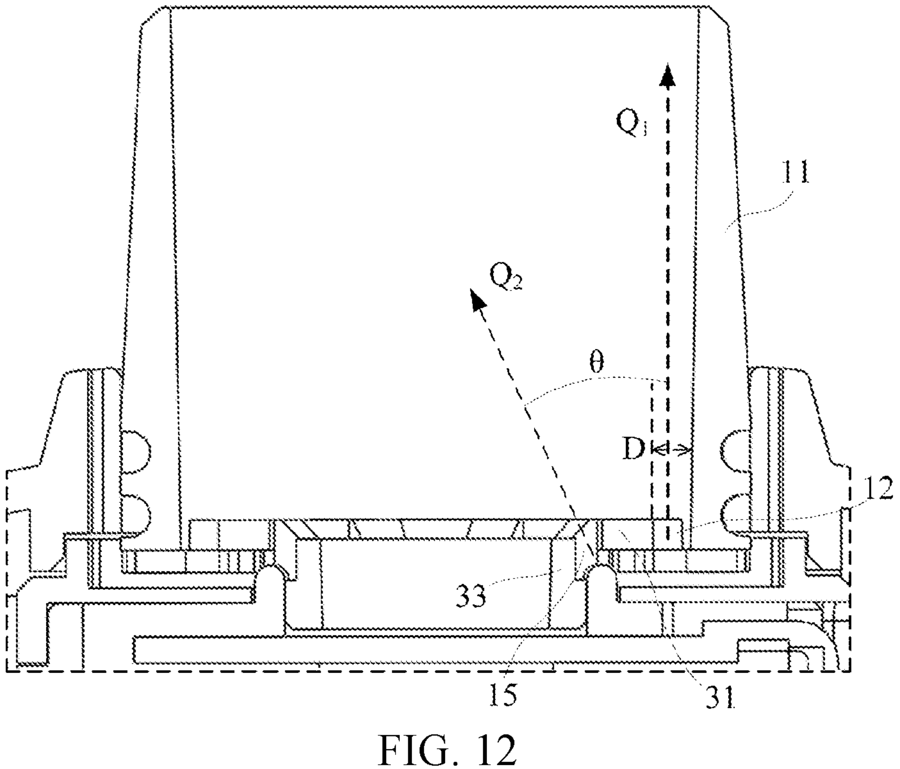
FIG. 12 is a schematic partial cross-sectional structural view of a first embodiment of a vaporizer from another perspective according to this application.

Referring to FIG. 12, FIG. 12 is a schematic partial cross-sectional structural view of a first embodiment of a vaporizer from another perspective according to this application. Airflow conditions in the first air inlet channel 12 and the second air inlet channel 15 in this exemplary embodiment are described below.

According to an aspect, a cross-sectional area of the first air inlet channel 12 affects an amount of the blocking airflow. Specifically, in a case that the air pressure difference caused by user's inhalation is fixed, within a specific range, a greater cross-sectional area of the first air inlet channel 12 indicates a greater amount of the blocking airflow. To be specific, a greater distance D between the first airflow guide portion 31 and the inner wall of the vaporization suction nozzle (that is, the inner wall of the airflow channel 11) indicates a greater cross-sectional area of the first air inlet channel 12 and a greater amount of the blocking airflow.

It may be understood that, since the air pressure difference caused by user's inhalation is limited, there is an upper limit of the amount of the blocking airflow. When the amount of the blocking airflow reaches the upper limit, the amount of the blocking airflow may not increase significantly even if the distance between the first airflow guide portion 31 and the inner wall of the vaporization suction nozzle continues to be increased.

According to another aspect, a flow direction of an airflow (as shown by an arrow Q2 in FIG. 12, which is the same below) entering the airflow channel 11 (that is, the vaporization suction nozzle) through the second air inlet channel 15 affects airflow conditions in the airflow channel 11. Specifically, when an angle (as shown by an angle θ in FIG. 12, which is the same below) between the flow direction of the airflow entering through the second air inlet channel 15 and a preset direction is excessively small, the airflow entering through the second air inlet channel 15 is affected and drawn by the blocking airflow. As a result, the airflow entering through the second air inlet channel 15 cannot be outputted well with the vapor, and the effect of speeding up discharging of the vapor is greatly weakened. In addition, when the angle between the flow direction of the airflow entering through the second air inlet channel 15 and the preset direction is excessively large, the airflow entering through the second air inlet channel 15 blocks an output path of the vapor, preventing the vapor from being conveyed to the air outlet 13 of the vaporization suction nozzle. The preset direction is parallel to a flow direction of the blocking airflow (as shown by an arrow Q1 in FIG. 12), that is, the preset direction may be represented by the flow direction of the blocking airflow.

In view of this, the angle between the flow direction of the airflow entering through the second air inlet channel 15 and the preset direction preferably ranges from 30° to 45°, for example, may be 30°, 33°, 37°, 41°, 43°, or 45°. In this way, it can be ensured that the airflow entering through the second air inlet channel 15 can be outputted with the vapor, to speed up discharging of the vapor.

It should be noted that, the flow direction of the airflow entering through the second air inlet channel 15 may be adjusted by adjusting the structure of the vaporization suction nozzle at a position of the second air inlet channel 15. For example, the flow direction of the airflow entering through the second air inlet channel 15 may be adjusted by adjusting positions of the first airflow guide portion 31 and the second airflow guide portion 33 in an axial direction of the airflow channel 11, which is not limited herein.

Figure 13:
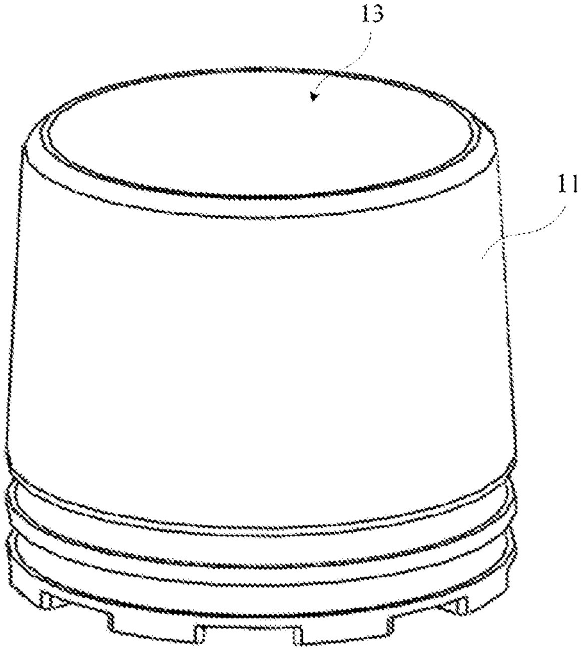
FIG. 13 is a schematic structural diagram of a fourth embodiment of a vaporization suction nozzle according to this application.
Figure 14:
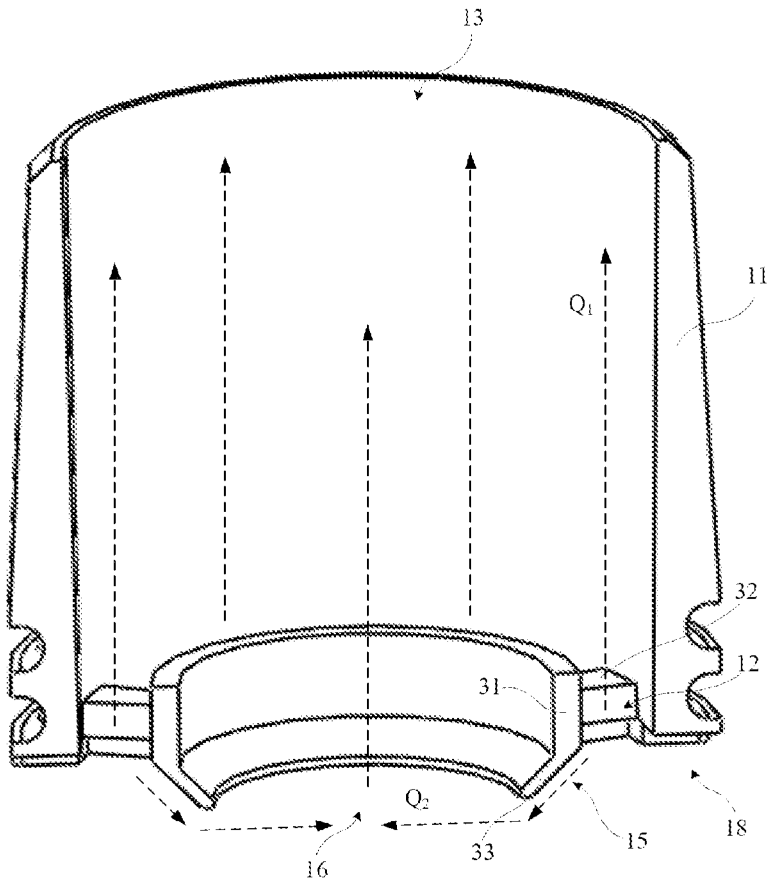
FIG. 14 is a schematic cross-sectional structural view of a fourth embodiment of a vaporization suction nozzle according to this application.

Referring to FIG. 13 and FIG. 14, FIG. 13 is a schematic structural diagram of a fourth embodiment of a vaporization suction nozzle according to this application, and FIG. 14 is a schematic cross-sectional structural view of a fourth embodiment of a vaporization suction nozzle according to this application.

The following describes an exemplary embodiment in which an air-curtain forming structure is a vaporization suction nozzle applicable to an electronic vaporization device. The vaporization suction nozzle is provided with a first air inlet 16, a second air inlet 18, and an air outlet 13, where the first air inlet 16 and the air outlet 13 are provided opposite to each other. The vaporization suction nozzle further includes an airflow guide member. The airflow guide member is in communication with the second air inlet 18, and the airflow guide member is configured to guide an airflow entering through the second air inlet 18 to flow toward the first air inlet 16. Detailed descriptions are provided below.

In this embodiment, the air-curtain forming structure is in the form of a vaporization suction nozzle. The vaporization suction nozzle provided in this embodiment may be applicable to electronic vaporization devices such as an e-cigarette and a medical vaporization electronic device.

Specifically, referring to FIG. 14, the vaporization suction nozzle includes an airflow channel 11, and the airflow channel 11 is configured to convey vapor. The vaporization suction nozzle further includes a first air inlet channel 12. The first air inlet channel 12 is in communication with the airflow channel 11, and the first air inlet channel 12 is configured to introduce an external airflow into the airflow channel 11, to form a blocking airflow (as shown by an arrow Q1 in FIG. 14, which is the same below) between an inner wall of the airflow channel 11 and the vapor. The blocking airflow forms an air curtain.

Further, the vaporization suction nozzle is further provided with a first air inlet 16 and an air outlet 13. The first air inlet 16 and the air outlet 13 are provided opposite to each other and in communication with the airflow channel 11 respectively. Vapor enters the airflow channel 11 through the first air inlet 16 and is conveyed to the air outlet 13 through the airflow channel 11, and then the vapor is outputted from the air outlet 13 for a user to inhale. The first air inlet channel 12 is close to the inner wall of the airflow channel 11, and an exit of the first air inlet channel 12 faces the air outlet 13, to ensure that the airflow entering the airflow channel 11 through the first air inlet channel 12 can flow along the inner wall of the airflow channel 11 (that is, the inner wall of the vaporization suction nozzle). That is, the blocking airflow is formed to block the vapor and the inner wall of the airflow channel 11, namely, to block the vapor and the inner wall of the vaporization suction nozzle, so that the vapor may be in contact with the inner wall of the vaporization suction nozzle as little as possible, thereby alleviating the problem of vapor condensation and reducing condensate formation.

Further, a flow direction of the blocking airflow is parallel to the inner wall of the airflow channel 11. That is, the flow direction of the blocking airflow is parallel to the inner wall of the vaporization suction nozzle, to ensure a favorable effect of the blocking airflow for blocking the vapor and the inner wall of the vaporization suction nozzle.

In an embodiment, still referring to FIG. 14, the vaporization suction nozzle is further provided with a second air inlet 18 different from the first air inlet 16, and the second air inlet 18 is configured to guide an external airflow to enter the vaporization suction nozzle. The vaporization suction nozzle further includes an airflow guide member. The airflow guide member is in communication with the second air inlet 18, and the airflow guide member is configured to guide the airflow entering through the second air inlet 18 to flow toward the first air inlet 16, and then carry vapor entering the vaporization suction nozzle through the first air inlet 16 to be outputted from the air outlet 13 of the vaporization suction nozzle, so that the user can inhale the vapor and discharging of the vapor can be sped up.

Specifically, at least a part of the airflow guide member is obliquely arranged in a direction away from the inner wall of the vaporization suction nozzle (that is, the inner wall of the airflow channel 11) and the air outlet 13, to guide the airflow entering through the second air inlet 18 to flow toward the first air inlet 16, and further carry the vapor entering the vaporization suction nozzle through the first air inlet 16 to be outputted from the air outlet 13 of the vaporization suction nozzle, so that the user can inhale the vapor and discharging of the vapor can be sped up.

In an embodiment, the airflow guide member includes a first airflow guide portion 31. The first air inlet channel 12 is formed between the first airflow guide portion 31 and the inner wall of the airflow channel 11 (that is, the inner wall of the vaporization suction nozzle), and the first airflow guide portion is configured to guide an airflow introduced through the first air inlet channel 12 to flow along the inner wall of the airflow channel 11, where the airflow entering through the first air inlet channel 12 is used to form a blocking airflow (as shown by an arrow Q1 in FIG. 14, which is the same below) between the inner wall of the vaporization suction nozzle and the vapor.

Further, the vaporization suction nozzle further includes a second connection portion 32. The first airflow guide portion 31 is connected to the inner wall of the airflow channel 11 through the second connection portion 32.

Figure 15:
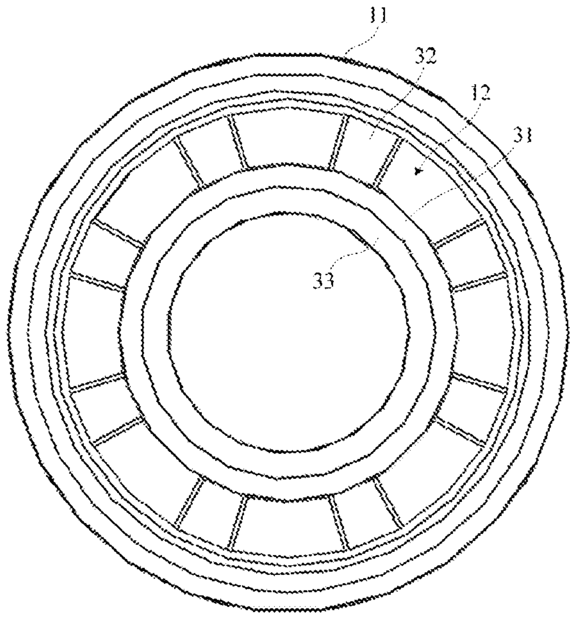
FIG. 15 is a schematic top structural view of a fourth embodiment of a vaporization suction nozzle according to this application.

Specifically, referring to FIG. 15, a plurality of second connection portions 32 are arranged between the first airflow guide portion 31 and the inner wall of the airflow channel 11. The plurality of second connection portions 32 are arranged at intervals sequentially in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channel 12 between the first airflow guide portion 31 and the inner wall of the airflow channel 11 is also ensured.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 14, the airflow guide member further includes a second airflow guide portion 33. The second airflow guide portion 33 is arranged on one side of the first airflow guide portion 31 away from the air outlet 13, that is, the first airflow guide portion 31 is closer to the air outlet 13 relative to the second airflow guide portion 33. The second airflow guide portion 33 is obliquely arranged in a direction away from the inner wall of the airflow channel 11 and the air outlet 13 to form the second air inlet channels 15, and an airflow (as shown by an arrow Q2 in FIG. 14, which is the same below) entering through the second air inlet channel 15 is used to guide the vapor to be outputted from the air outlet 13, thereby speeding up discharging of the vapor.

Specifically, the airflow entering through the second air inlet channel 15 flows to the first air inlet 16 along the second airflow guide portion 33 to be mixed with vapor at the first air inlet 16, and then carries the vapor to pass through the first air inlet 16 and to be outputted from the air outlet 13.

Optionally, the second airflow guide portion 33 may be in an annular shape corresponding to an inner space of the vaporization suction nozzle, and surrounds in a circumferential direction of the vaporization suction nozzle.

It should be noted that, in this exemplary embodiment, the airflow guide member is arranged at one end of the vaporization suction nozzle away from the air outlet 13, so that the airflow guide member is close to the vaporization core of the electronic vaporization device as much as possible after the vaporization suction nozzle is assembled to the electronic vaporization device. In this way, the airflow guided by the airflow guide member can drive the output of the vapor near the vaporization core to the greatest extent, and the problem of vapor retention near the vaporization core can be alleviated to the greatest extent, thereby alleviating the problem of vapor condensation near the vaporization core to the greatest extent.

Certainly, in some other embodiments of this application, the airflow guide member and the second air inlet 18 in communication with the airflow guide member may be arranged at other positions in the axial direction of the vaporization suction nozzle, and the objective of alleviating the problem of vapor retention near the vaporization core can also be achieved, which is not limited herein.

Figure 16:
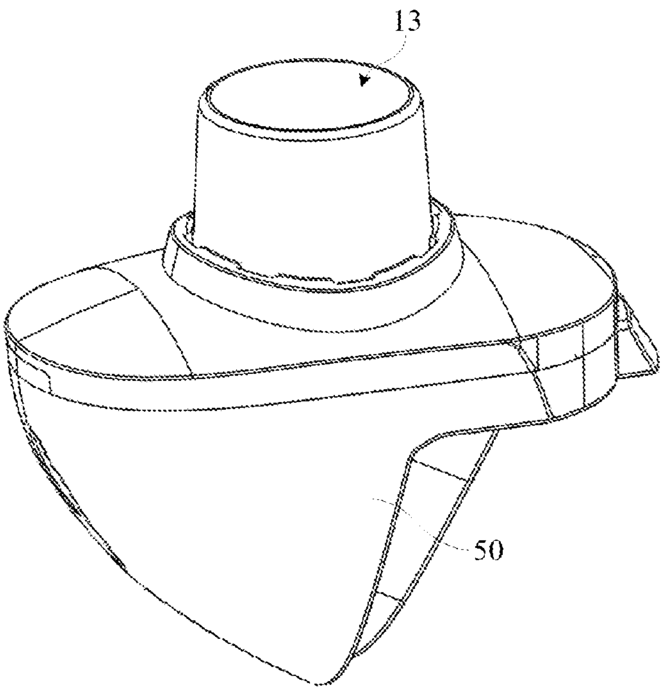
FIG. 16 is a schematic structural diagram of a second embodiment of a vaporizer according to this application.
Figure 16:
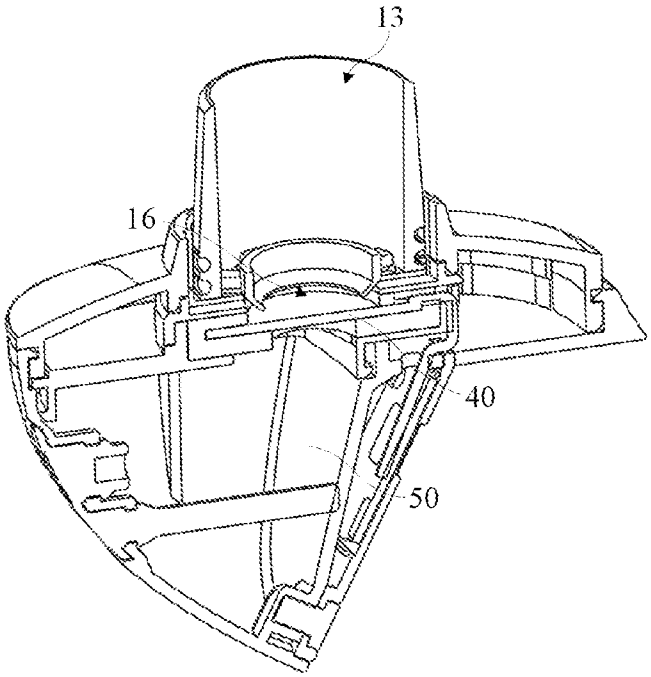
Figure 17:
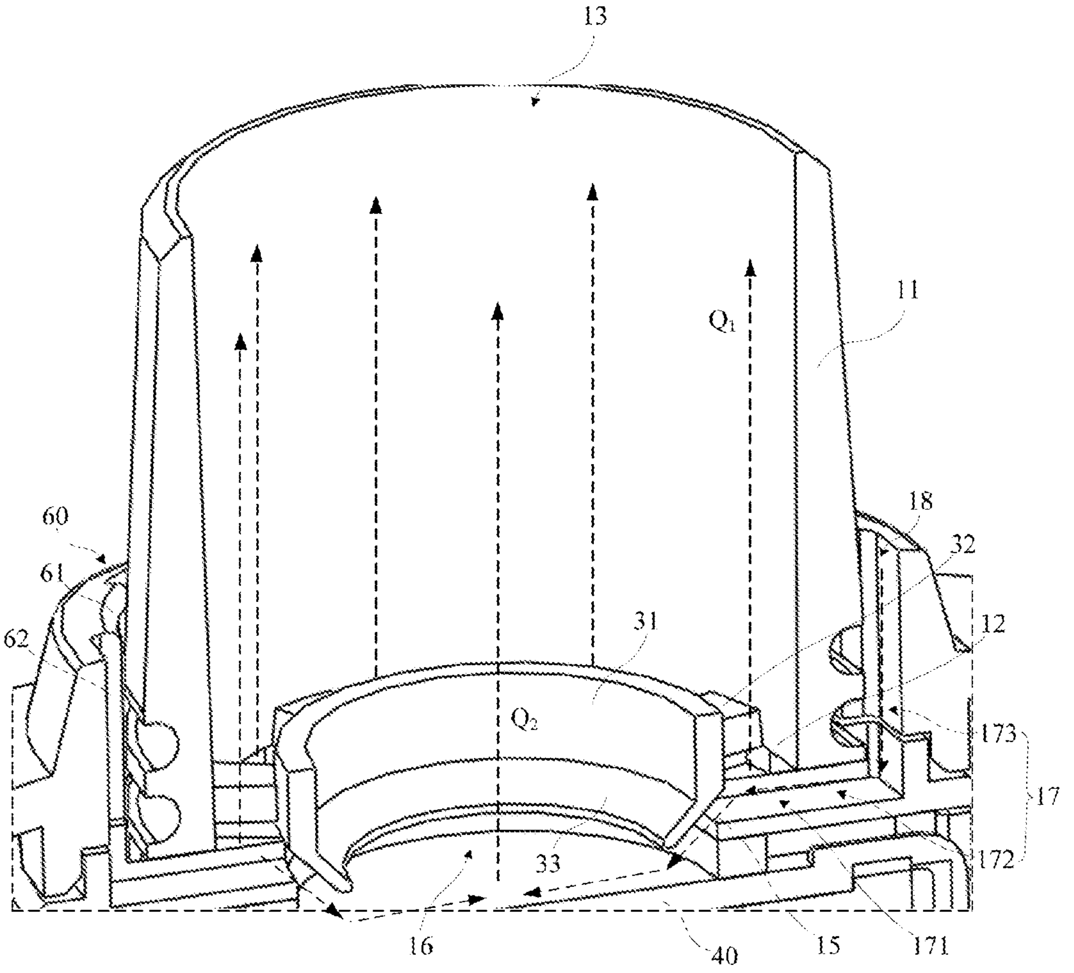
FIG. 17 is a schematic partial cross-sectional structural view of a second embodiment of a vaporizer according to this application.

Referring to FIG. 16 and FIG. 17, FIG. 16 is a schematic structural diagram of a second embodiment of a vaporizer according to this application, and FIG. 17 is a schematic partial cross-sectional structural view of a second embodiment of a vaporizer according to this application.

The following describes an exemplary embodiment in which an air-curtain forming structure is a vaporizer applicable to an electronic vaporization device.

In this embodiment, the air-curtain forming structure is in the form of a vaporizer. The vaporizer provided in this embodiment may be applicable to electronic vaporization devices such as an e-cigarette and a medical vaporizer. FIG. 16 shows a situation in which the air-curtain forming structure is applicable to a medical vaporizer, which is merely used for description and is not intended to constitute a limitation to an application environment of the air-curtain forming structure in this embodiment.

In this embodiment, referring to FIG. 16, the air-curtain forming structure includes a vaporization suction nozzle, a vaporization core 40, and a liquid storage cavity 50. The vaporization suction nozzle is provided with a first air inlet 16 and an air outlet 13, vapor enters the vaporization suction nozzle through the first air inlet 16 and is conveyed to the air outlet 13 through the vaporization suction nozzle, and then the vapor is outputted from the air outlet 13 for a user to inhale. The vaporization core 40 is arranged at a position of the first air inlet 16 of the vaporization suction nozzle and is configured to vaporize an aerosol-generation substrate stored in the liquid storage cavity 50 to generate vapor. A vapor generation device of the air-curtain forming structure in this embodiment includes structures such as the vaporization core 40 and the liquid storage cavity 50, and is configured to generate vapor.

For the situation in which the air-curtain forming structure in this embodiment is applicable to a medical vaporizer, the vaporization core 40 may be an ultrasonic vaporization sheet, and the ultrasonic vaporization sheet vaporizes the aerosol-generation substrate through high-frequency oscillation to generate vapor. The specific principle thereof falls within the scope understood by a person skilled in the art, and details are not described herein again. Certainly, for situations in which the air-curtain forming structure is applicable to other fields, the vaporization core 40 may also heat and vaporize the aerosol-generation substrate to generate vapor, which is not limited herein.

Specifically, referring to FIG. 17, the vaporization suction nozzle includes an airflow channel 11, and the airflow channel 11 is configured to convey vapor. The vaporization suction nozzle further includes a first air inlet channel 12. The first air inlet channel 12 is in communication with the airflow channel 11, and the first air inlet channel 12 is configured to introduce an external airflow into the airflow channel 11, to form a blocking airflow (as shown by an arrow Q1 in FIG. 17, which is the same below) between an inner wall of the airflow channel 11 and the vapor. The blocking airflow forms an air curtain.

Further, the first air inlet 16 and the air outlet 13 are provided opposite to each other and are in communication with the airflow channel 11 respectively. The first air inlet channel 12 is close to the inner wall of the airflow channel 11, and an exit of the first air inlet channel 12 faces the air outlet 13, to ensure that the airflow entering the airflow channel 11 through the first air inlet channel 12 can flow along the inner wall of the airflow channel 11 (that is, the inner wall of the vaporization suction nozzle). That is, the blocking airflow is formed to block the vapor and the inner wall of the airflow channel 11, namely, to block the vapor and the inner wall of the vaporization suction nozzle, so that the vapor may be in contact with the inner wall of the vaporization suction nozzle as little as possible, thereby alleviating the problem of vapor condensation and reducing condensate formation.

Further, a flow direction of the blocking airflow is parallel to the inner wall of the airflow channel 11. That is, the flow direction of the blocking airflow is parallel to the inner wall of the vaporization suction nozzle, to ensure a favorable effect of the blocking airflow for blocking the vapor and the inner wall of the vaporization suction nozzle.

In an embodiment, still referring to FIG. 17, the vaporization suction nozzle is further provided with a second air inlet 18 different from the first air inlet 16, and the second air inlet 18 is configured to guide an external airflow to enter the vaporization suction nozzle. The vaporization suction nozzle further includes an airflow guide member. The airflow guide member is in communication with the second air inlet 18, and the airflow guide member is configured to guide the airflow entering through the second air inlet 18 to flow toward the first air inlet 16, and then carry vapor entering the vaporization suction nozzle through the first air inlet 16 to be outputted from the air outlet 13 of the vaporization suction nozzle, so that the user can inhale the vapor and discharging of the vapor can be sped up.

That is, the airflow guide member is configured to guide the airflow to flow toward the vaporization core 40, to drive the vapor near the vaporization core 40 to be outputted from the air outlet 13, so that the problem of vapor retention near the vaporization core 40 can be effectively alleviated, thereby further alleviating the problem of vapor condensation near the vaporization core 40.

Specifically, at least a part of the airflow guide member is obliquely arranged in a direction away from the inner wall and the vaporization suction nozzle and the air outlet 13, to guide the airflow entering through the second air inlet 18 to flow toward the first air inlet 16, that is, to guide the airflow to flow toward the vaporization core 40 to directly face a surface of the vaporization core 40, so as to carry vapor formed by the vaporization core 40 through vaporization to enter the vaporization suction nozzle through the first air inlet 16 and to be outputted from the air outlet 13, and speed up discharging of the vapor. Therefore, vapor in contact with the inner wall of the vaporization suction nozzle can be reduced to some extent, thereby further alleviating the problem vapor condensation and reducing condensate formation.

In an embodiment, still referring to FIG. 17, the airflow guide member includes a first airflow guide portion 31. The first air inlet channel 12 is formed between the first airflow guide portion 31 and the inner wall of the airflow channel 11 (that is, the inner wall of the vaporization suction nozzle), and the first airflow guide portion is configured to guide an airflow introduced through the first air inlet channel 12 to flow along the inner wall of the airflow channel 11, where the airflow entering through the first air inlet channel 12 is used to form a blocking airflow between the inner wall of the vaporization suction nozzle and the vapor.

Further, the vaporization suction nozzle further includes a second connection portion 32. The first airflow guide portion 31 is connected to the inner wall of the airflow channel 11 through the second connection portion 32.

Specifically, a plurality of second connection portions 32 are arranged between the first airflow guide portion 31 and the inner wall of the airflow channel 11. The plurality of second connection portions 32 are arranged at intervals sequentially in a circumferential direction of the first airflow guide portion 31, and the first air inlet channel 12 is formed between adjacent second connection portions 32, that is, at least one first air inlet channel 12 is formed. In this way, a relative position of the first airflow guide portion 31 in the vaporization suction nozzle is fixed, and formation of the first air inlet channel 12 between the first airflow guide portion 31 and the inner wall of the airflow channel 11 is also ensured.

Optionally, the first airflow guide portion 31 may be in an annular shape corresponding to an inner space of the vaporization suction nozzle, and surrounds in a circumferential direction of the vaporization suction nozzle.

In an embodiment, still referring to FIG. 17, the airflow guide member further includes a second airflow guide portion 33. The second airflow guide portion 33 is arranged on one side of the first airflow guide portion 31 away from the air outlet 13, that is, the first airflow guide portion 31 is closer to the air outlet 13 relative to the second airflow guide portion 33. The second airflow guide portion 33 is obliquely arranged in a direction away from the inner wall of the airflow channel 11 and the air outlet 13 to form the second air inlet channels 15, and an airflow entering through the second air inlet channel 15 is used to guide the vapor to be outputted from the air outlet 13, thereby speeding up discharging of the vapor.

Specifically, the airflow entering through the second air inlet channel 15 flows to the first air inlet 16 along the second airflow guide portion 33 to be mixed with vapor at the first air inlet 16, and then carries the vapor to pass through the first air inlet 16 and to be outputted from the air outlet 13.

Optionally, the second airflow guide portion 33 may be in an annular shape corresponding to an inner space of the vaporization suction nozzle, and surrounds in a circumferential direction of the vaporization suction nozzle.

In an embodiment, still referring to FIG. 17, the air-curtain forming structure further includes a converging channel 17, one end of the converging channel 17 is an air inlet, that is, a second air inlet 18, and the other end of the converging channel is a diverging opening 171, where the diverging opening 171 is in communication with the first air inlet channel 12 and the second air inlet channel 15 respectively.

Specifically, the converging channel 17 includes a first channel section 172 and a second channel section 173 that are in communication with each other, an end opening of the first channel section 172 away from the second channel section 173 is the diverging opening 171, and an end opening of the second channel section 173 away from the first channel section 172 is the air inlet, that is, the second air inlet 18. An extending direction of the first channel section 172 is different from an extending direction of the second channel section 173.

FIG. 17 shows that the extending direction of the first channel section 172 is a horizontal direction, the extending direction of the second channel section 173 is a vertical direction, and the second channel section 173 extends toward the air outlet 13. When the user performs inhalation, an external airflow enters the second channel section 173 through the second air inlet 18 and is conveyed to the first channel section 172, and then the airflow passes through the diverging opening 171 and enters the airflow channel 11 in the vaporization suction nozzle through the first air inlet channel 12 and the second air inlet channel 15 respectively, where flow conditions of airflows are shown by dashed-line arrows in FIG. 17.

Further, the air-curtain forming structure is provided with a mounting portion 60. The mounting portion 60 is provided with a mounting protrusion 61 and a vent groove 62, where the mounting protrusion 61 is configured to fix the vaporization suction nozzle. After the vaporization suction nozzle is fixed to the mounting portion 60, the first channel section 172 is formed between the vaporization suction nozzle and the mounting portion 60, and to be specific, the first channel section 172 is formed between the vaporization suction nozzle and a bottom portion of the mounting portion 60. In addition, the second channel section 173 is formed between the vent groove 62 and the vaporization suction nozzle.

Figure 18:
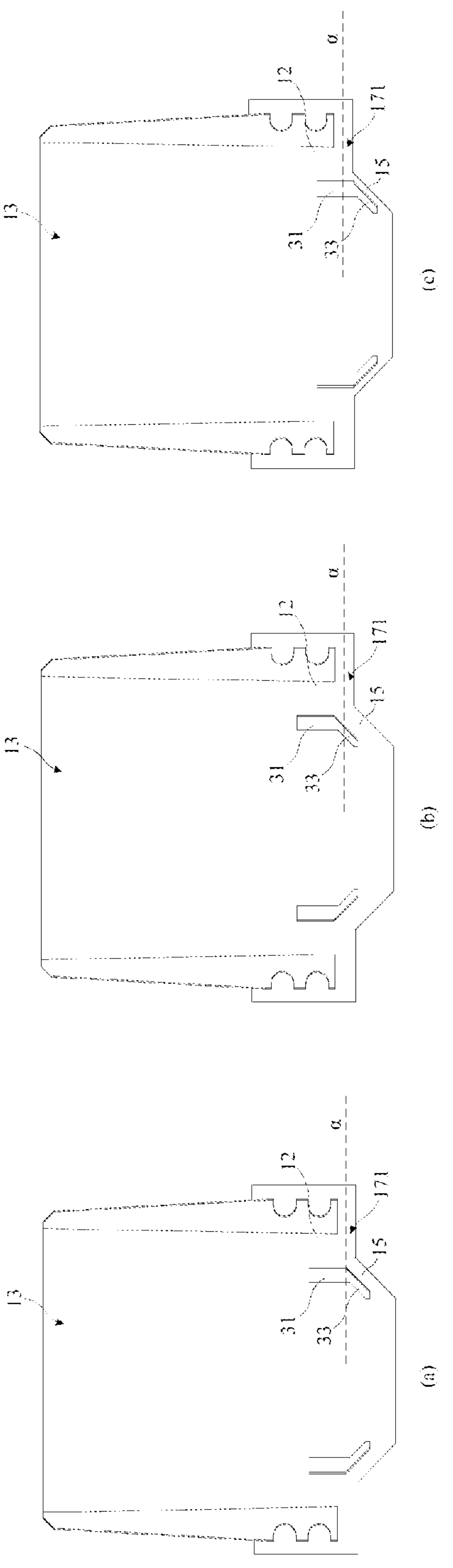
FIG. 18 is a schematic structural diagram of a relative position relationship between a center line of a diverging opening and a joint of a first airflow guide portion and a second airflow guide portion of a vaporizer according to this application.

Referring to FIG. 18, FIG. 18 is a schematic structural diagram of a relative position relationship between a center line of a diverging opening and a joint of a first airflow guide portion and a second airflow guide portion of a vaporizer according to this application. Airflow conditions in the first air inlet channel 12 and the second air inlet channel 15 in this exemplary embodiment are described below.

In this exemplary embodiment, the airflow entering through the first air inlet channel 12 forms the blocking airflow between the inner wall of the vaporization suction nozzle and the vapor, so that the vapor is in contact with the inner wall of the vaporization suction nozzle as little as possible, thereby alleviating the problem of vapor condensation and reducing condensate generation. In addition, the airflow entering through the second air inlet channel 15 guides the vapor to be outputted from the air outlet 13, to speed up discharging of the vapor, thereby effectively alleviating the problem of vapor condensation in a cavity encircled by the airflow guide member.

Since the air pressure difference caused by user's inhalation is fixed, a total amount of airflows entering the first air inlet channel 12 and the second air inlet channel 15 is fixed. Therefore, in this exemplary embodiment, the amounts of the airflows entering the first air inlet channel 12 and the second air inlet channel 15 are appropriately allocated, to alleviate the problem of vapor condensation on the inner wall of the vaporization suction nozzle and vapor condensation in the cavity encircled by the airflow guide member.

In an embodiment, as shown in FIG. 18*a*, a center line a of the diverging opening 171 (the center line a of the diverging opening 171 is defined as a central axis perpendicular to the diverging opening 171, which is the same below) extends through the joint of the first airflow guide portion 31 and the second airflow guide portion 33. In this way, the airflow entering through the first air inlet channel 12 is sufficient to form a blocking airflow between the inner wall of the vaporization suction nozzle and the vapor, so that the adhesion degree of the vapor on the inner wall of the vaporization suction nozzle is reduced. In addition, the airflow entering through the second air inlet channel 15 is sufficient to quickly carry the vapor to be discharged, so that the adhesion degree of the vapor in the cavity encircled by the airflow guide member can be reduced.

In an alternative embodiment, as shown in FIG. 18*b*, the center line a of the diverging opening 171 is away from the air outlet 13 relative to the joint of the first airflow guide portion 31 and the second airflow guide portion 33. In this way, the amount of airflows entering through the second air inlet channel 15 is significantly increased, which can further speed up carrying the vapor to be discharged, and further reduce the adhesion degree of the vapor in the cavity encircled by the airflow guide member, thereby alleviating the problem of vapor condensation in the cavity encircled by the airflow guide member.

In another alternative embodiment, as shown in FIG. 18*c*, the center line a of the diverging opening 171 is closer to the air outlet 13 relative to the joint of the first airflow guide portion 31 and the second airflow guide portion 33. In this way, the amount of airflows entering through the first air inlet channel 12 is significantly increased, which can further increase an amount of blocking airflows between the inner wall of the vaporization suction nozzle and the vapor, and further reduce the adhesion degree of the vapor on the inner wall of the vaporization suction nozzle, thereby alleviating the problem of vapor condensation on the inner wall of the vaporization suction nozzle.

It should be noted that, a size relationship between the cross-sectional areas of the first air inlet channel 12 and the second air inlet channel 15 is the same as a magnitude relationship between the amount of airflows in the first air inlet channel 12 and the amount of airflows in the second air inlet channel 15. That is, if the cross-sectional area of the first air inlet channel 12 is greater than the cross-sectional area of the second air inlet channel 15, the amount of airflows in the first air inlet channel 12 is greater than that in the second air inlet channel 15, and vice versa.

In view of this, in this exemplary embodiment, the cross-sectional area of the second air inlet channel 15 may be adjusted by adjusting an inclination degree of the second airflow guide portion 33 of the airflow guide member, to adjust the size relationship between the cross-sectional areas of the first air inlet channel 12 and the second air inlet channel 15, thereby adjusting the amount of airflows in the first air inlet channel 12 and the amount of airflows in the second air inlet channel 15.

Specifically, the second airflow guide portion 33 being more inclined in a direction away from the air outlet 13 indicates a smaller cross-sectional area of the second air inlet channel 15, which indicates a smaller amount of airflows in the second air inlet channel 15 and a greater amount of airflows in the first air inlet channel 12, and vice versa.

It should be noted that, according to the foregoing method, the adhesion degree of the vapor on the inner wall of the vaporization suction nozzle and the adhesion degree of the vapor in the cavity encircled by the airflow guide member are less than 3%. It can be seen that, based on the design of the first air inlet channel 12 and the second air inlet channel 15 in this exemplary embodiment, the adhesion degree of the vapor can be effectively reduced, thereby alleviating the problem of vapor condensation.

Figure 19:
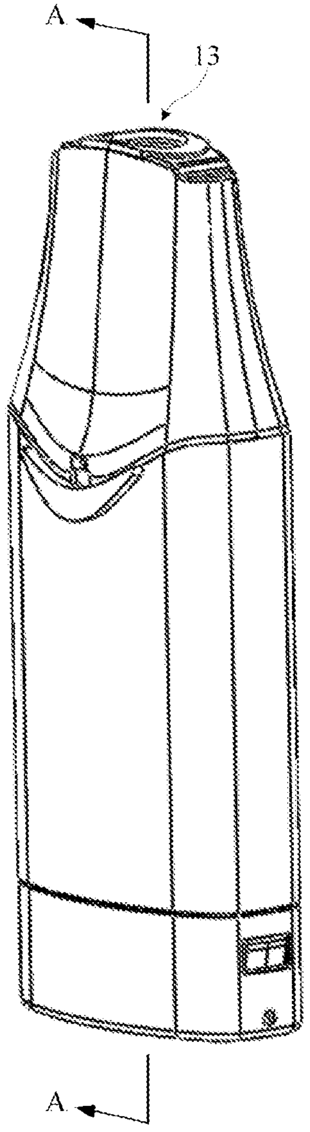
FIG. 19 is a schematic structural diagram of a third embodiment of a vaporizer according to this application.
Figure 20:
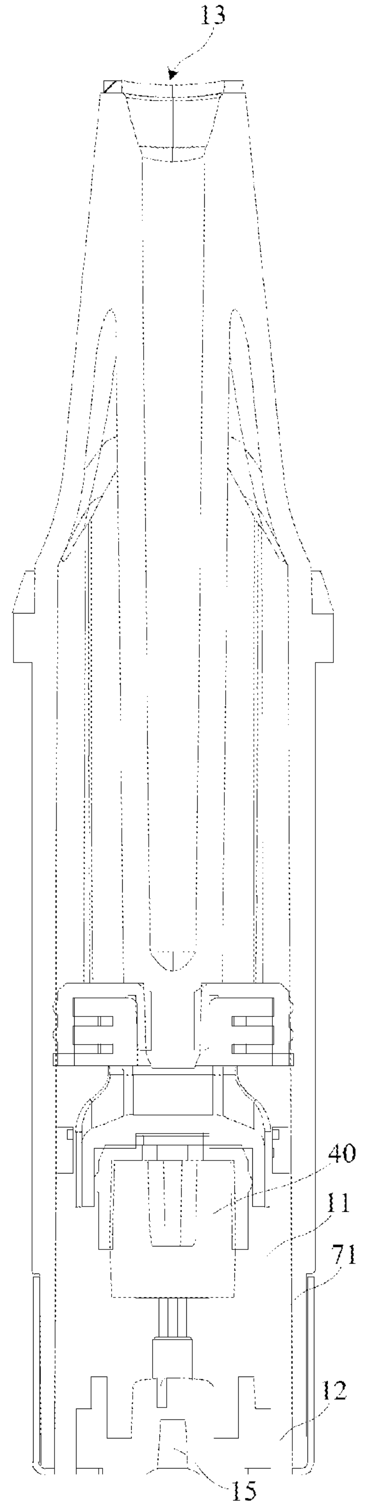
FIG. 20 is a schematic cross-sectional structural view of a third embodiment of a vaporizer in a direction A-A according to this application.

Referring to FIG. 19 and FIG. 20, FIG. 19 is a schematic structural diagram of a third embodiment of a vaporizer according to this application, and FIG. 20 is a schematic cross-sectional structural view of a third embodiment of a vaporizer in a direction A-A according to this application.

The following describes an exemplary embodiment in which an air-curtain forming structure is a vaporizer applicable to an electronic vaporization device.

In this embodiment, the air-curtain forming structure is in the form of a vaporizer. The vaporizer provided in this embodiment may be applicable to electronic vaporization devices such as an e-cigarette and a medical vaporizer. FIG. 19 shows a situation in which the air-curtain forming structure is applicable to an e-cigarette, which is merely used for description and is not intended to constitute a limitation to an application environment of the air-curtain forming structure in this embodiment.

Specifically, the vaporizer includes an airflow channel 11, and the airflow channel 11 is configured to convey vapor. The vaporizer further includes a first air inlet channel 12. The first air inlet channel 12 is in communication with the airflow channel 11, and the first air inlet channel 12 is configured to introduce an external airflow into the airflow channel 11, to form a blocking airflow between an inner wall of the airflow channel 11 and the vapor. The blocking airflow forms an air curtain.

Further, the vaporizer further includes an air outlet 13 in communication with the airflow channel 11, the first air inlet channel 12 is close to the inner wall of the airflow channel 11, and an exit of the first air inlet channel 12 faces the air outlet 13, to ensure that the airflow entering the airflow channel 11 through the first air inlet channel 12 can flow along the inner wall of the airflow channel 11 (that is, an inner wall of the vaporizer). That is, the blocking airflow is formed to block the vapor and the inner wall of the airflow channel 11, namely, to block the vapor and the inner wall of the vaporizer, so that the vapor may be in contact with the inner wall of the vaporizer as little as possible, thereby alleviating the problem of vapor condensation and reducing condensate formation.

In an embodiment, still referring to FIG. 20, the vaporizer further includes a vaporization cavity 71. A vaporization core 40 is arranged in the vaporization cavity 71 and configured to vaporize an aerosol-generation substrate to form vapor. The airflow channel 11 is provided in the vaporization cavity 71, that is, a space used for accommodating vapor in the vaporization cavity 71 is the airflow channel 11. The first air inlet channel 12 is provided at a position on a bottom portion of the vaporization cavity 71 close to an inner wall of the vaporization cavity 71, so that an airflow entering the vaporization cavity 71 through the first air inlet channel 12 flows through the inner wall of the vaporization cavity 71 during inhalation by a user, thereby forming a blocking airflow between the inner wall of the vaporization cavity 71 and the vapor.

Further, the vaporizer further includes a second air inlet channel 15, an airflow entering through the second air inlet channel 15 is used to guide the vapor to be outputted from the air outlet 13, to speed up discharging of the vapor, so that the vapor in contact with the inner wall of the vaporization cavity 71 can also be reduced to some extent, and the problem of vapor condensation can also be alleviated. Specifically, the second air inlet channel 15 is provided on the bottom portion of the vaporization cavity 71, and the first air inlet channel 12 is closer to an edge of the bottom portion of the vaporization cavity 71 relative to the second air inlet channel 15.

Figure 21:
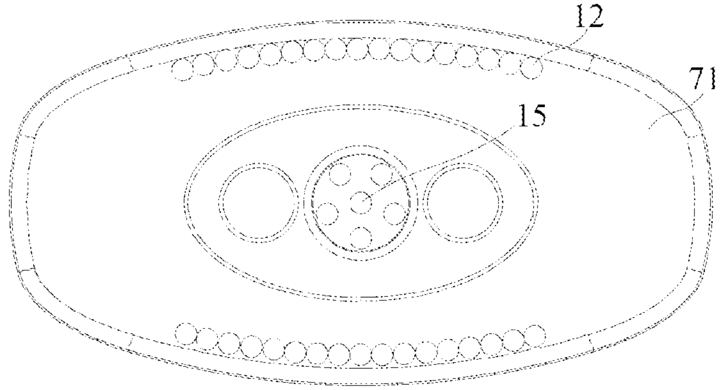
FIG. 21 is a schematic bottom structural view of a third embodiment of a vaporizer according to this application.
Figure 21:
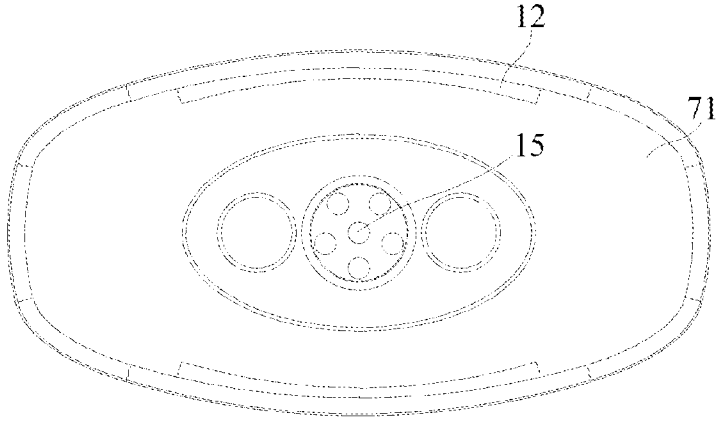

Still further, referring to FIG. 21, the first air inlet channels 12 are respectively provided on two opposite sides of the second air inlet channel 15. According to the foregoing method, a number of the first air inlet channels 12 can be increased, to further reduce contact between the vapor and the inner wall of the vaporization cavity 71, thereby further alleviating the problem of vapor condensation. In addition, the first air inlet channels 12 are provided on opposite sides of the second air inlet channel 15 as symmetrically as possible, so that the distribution of blocking airflows in the vaporization cavity 71 can be optimized, thereby improving the effect of alleviating the problem of vapor condensation.

In an embodiment, as shown in FIG. 21*a*, the first air inlet channel 12 may be in the form of a through hole. A plurality of first air inlet channels 12 that are arranged at intervals are provided on the position on the bottom portion of the vaporization cavity 71 close to the inner wall of the vaporization cavity 71, and airflows entering the vaporization cavity 71 through the first air inlet channels 12 in the form of a through hole form blocking airflows. Specifically, the plurality of first air inlet channels 12 are provided at intervals along an edge on the bottom portion of the vaporization cavity, and the plurality of first air inlet channels 12 that are arranged at intervals are provided on two opposite sides of the second air inlet channel 15.

Optionally, a hole diameter of the first air inlet channel 12 in the form of a through hole may be 0.3 mm or 0.4 mm, which is not limited herein.

In an alternative embodiment, a cross-section of the first air inlet channel 12 is strip-shaped, that is, as shown in FIG. 21*b*, the first air inlet channel 12 is a strip-shaped narrow gap. The first air inlet channel 12 in the form of a narrow gap extends along the edge on the bottom portion of the vaporization cavity 71, and airflows entering the vaporization cavity 71 through the first air inlet channels 12 in the form of a narrow gap form the blocking airflows. Further, the first air inlet channels 12 in the form of a narrow gap are respectively provided on two opposite sides of the second air inlet channel 15.

Optionally, a width of the first air inlet channel 12 in the form of a narrow gap may be 0.3 mm or 0.4 mm, which is not limited herein.

It should be noted that, a distribution condition of blocking airflows formed by the first air inlet channel 12 in the form of a narrow gap is better than a distribution condition of blocking airflows formed by the first air inlet channel 12 in the form of a through hole, and a distribution condition of blocking airflows formed by the first air inlet channel 12 in the form of a narrow gap whose width is 0.4 mm is better than a distribution condition of blocking airflows formed by the first air inlet channel 12 in the form of a narrow gap whose width is 0.3 mm. In addition, due to the existence of the blocking airflows, an entire flow direction of airflows inside the vaporization cavity 71 is more ordered, so that a vortex flow is unlikely to be formed.

Figure 22:
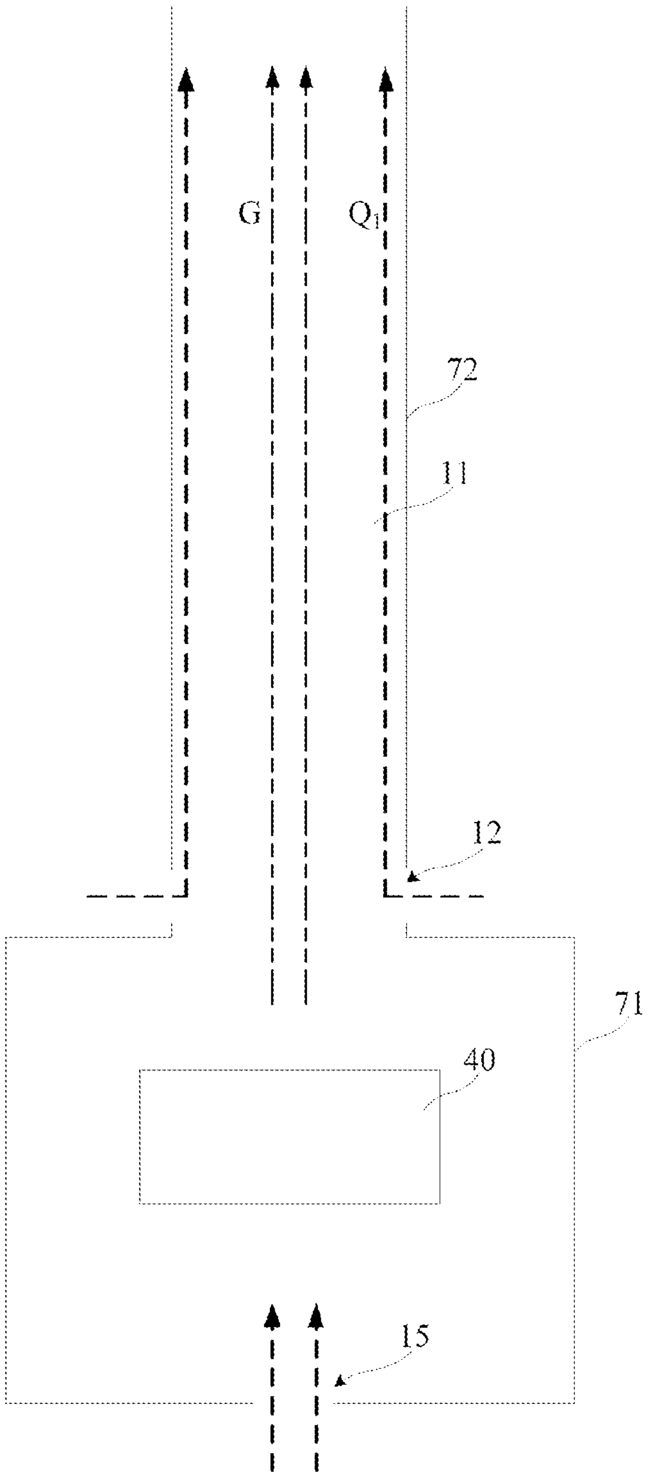
FIG. 22 is a schematic structural diagram of a fourth embodiment of a vaporizer according to this application.

Referring to FIG. 22, FIG. 22 is a schematic structural diagram of a fourth embodiment of a vaporizer according to this application.

The following describes an exemplary embodiment in which an air-curtain forming structure is a vaporizer applicable to an electronic vaporization device.

In this embodiment, the air-curtain forming structure is in the form of a vaporizer. The vaporizer provided in this embodiment may be applicable to electronic vaporization devices such as an e-cigarette and a medical vaporizer. FIG. 22 shows a situation in which the air-curtain forming structure is applicable to an e-cigarette, which is merely used for description and is not intended to constitute a limitation to an application environment of the air-curtain forming structure in this embodiment.

Specifically, the vaporizer includes an airflow channel 11, and the airflow channel 11 is configured to convey vapor. The vaporizer further includes a first air inlet channel 12. The first air inlet channel 12 is in communication with the airflow channel 11, and the first air inlet channel 12 is configured to introduce an external airflow into the airflow channel 11, to form a blocking airflow between an inner wall of the airflow channel 11 and the vapor. The blocking airflow forms an air curtain.

The vaporizer further includes an air outlet channel 72, the airflow channel 11 is provided in the air outlet channel 72, and the first air inlet channel 12 is provided on a side wall of the air outlet channel 72. When a user performs inhalation, an external airflow enters the air outlet channel 72 through the first air inlet channel 12 on the side wall of the air outlet channel 72 and then flows along an inner wall of the air outlet channel 72, to form a blocking airflow between the inner wall of the air outlet channel 72 and the vapor. Therefore, contact between high-temperature vapor in the air outlet channel 72 and the inner wall of the low-temperature air outlet channel 72 can be effectively reduced, and vapor condensation can be reduced. As shown in FIG. 22, blocking airflows Q1 are located between the inner wall of the air outlet channel 72 and the vapor G, to block the inner wall of the air outlet channel 72 and the vapor G.

Further, the vaporizer further includes a vaporization cavity 71 A vaporization core 40 is arranged in the vaporization cavity 71 and configured to vaporize an aerosol-generation substrate to form vapor. The vaporization cavity 71 is in communication with the air outlet channel 72. In addition, the vaporization cavity 71 is further provided with a second air inlet channel 15. When the user performs inhalation, an external airflow enters the vaporization cavity 71 through the second air inlet channel 15, to carry the vapor in the vaporization cavity 71 to be discharged through the air outlet channel 72, which can speed up discharging of the vapor. Therefore, contact between the vapor and the inner wall of the vaporization cavity 71 and contact between the vapor and the inner wall of the air outlet channel 72 can be reduced to some extent, and the problem of vapor condensation can also be alleviated.

As shown in FIG. 22, the first air inlet channel 12 is provided in a part of the air outlet channel 72 close to the vaporization cavity 71, so that vapor condensation occurred in the air outlet channel 72 between the first air inlet channel 12 and the vaporization cavity 71 can be avoided as much as possible, thereby further alleviating the problem of vapor condensation.

Figure 23:
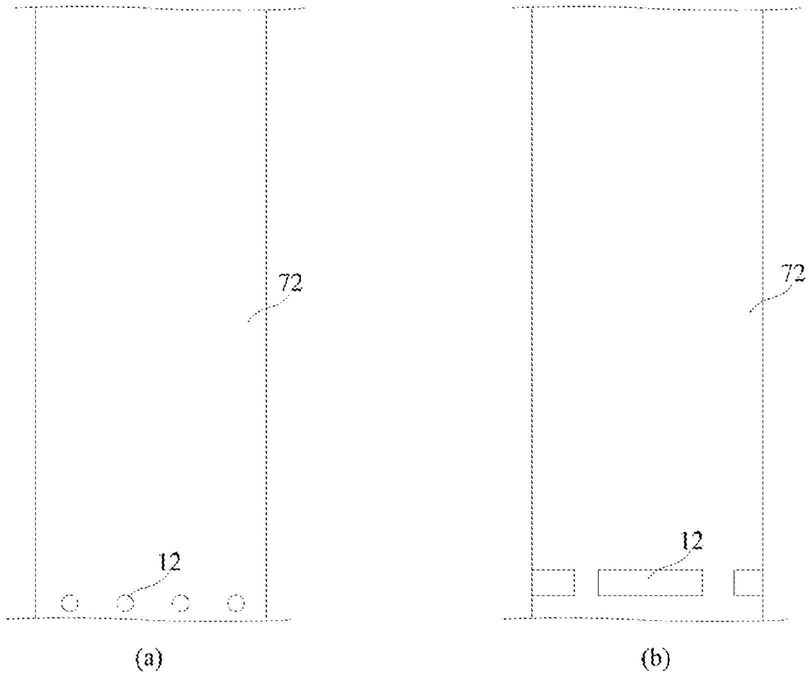
FIG. 23 is a schematic structural diagram of an embodiment of an air outlet channel according to this application.

Further, referring to FIG. 23, the vaporizer includes a plurality of first air inlet channels 12, where the plurality of first air inlet channels 12 are provided at intervals sequentially in a circumferential direction of the air outlet channel 72. Still further, the plurality of first air inlet channels 12 are provided at uniform intervals in the circumferential direction of the air outlet channel 72, so that airflows are uniformly introduced onto a side wall of the air outlet channel 72, thereby forming blocking airflows in the form of an air curtain that are well distributed in the air outlet channel 72.

Optionally, the first air inlet channel 12 is preferably a circular hole shown in FIG. 23*a* or an elongated hole shown in FIG. 23*b*. In addition, a diameter of the first air inlet channel 12 in the form of a circular hole may be 0.3 mm or 0.4 mm, and a width of the first air inlet channel 12 in the form of an elongated hole may be 0.3 mm or 0.4 mm, which are not limited herein.

Referring to the following table, the table shows an accumulation amount of condensate in a conventional air outlet channel and the air outlet channel 72 in this exemplary embodiment when the user performs inhalation for different times.

| | Accumulation amount of condensate/mg | | |
|---|---|---|---|
| | 10/times | 30/times | 50/times |
| Conventional air outlet channel | 1.1 | 2.2 | 4.8 |
| Air outlet channel in this exemplary embodiment | 0.8 | 1.9 | 4.7 |

Based on the above, an air-curtain forming structure applicable to an electronic vaporization device is provided in this application, and the air-curtain forming structure includes an airflow channel configured to convey vapor. The airflow channel includes a first air inlet channel, and the first air inlet channel is configured to introduce an external airflow into the airflow channel, to form a blocking airflow between an inner wall of the airflow channel insert and vapor. In this application, the blocking airflow is used to block the inner wall of the airflow channel and the vapor, so that the vapor is in contact with the inner wall of the airflow channel as little as possible. Therefore, the problem of vapor condensation can be alleviated, and formation of condensate can be reduced, thereby improving the use experience of a user, reducing dosage loss, and reducing a risk of liquid leakage.

Figure 24:
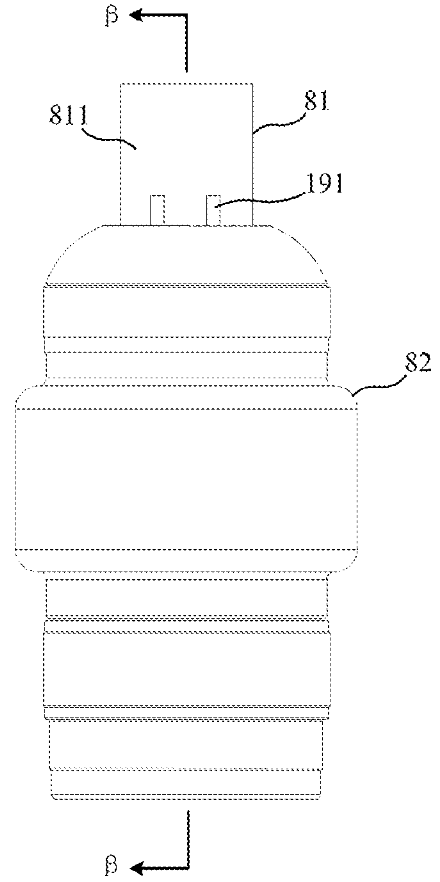
FIG. 24 is a schematic structural diagram of a fifth embodiment of a vaporizer according to this application.
Figure 25:
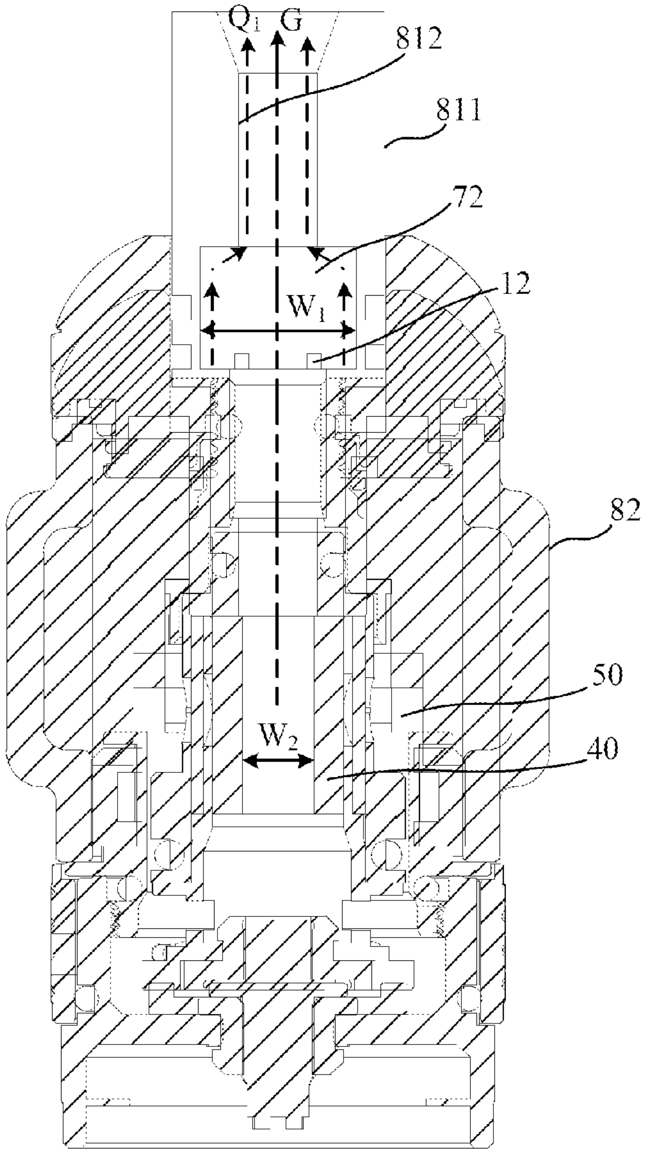
FIG. 25 is a schematic cross-sectional structural view of the vaporizer shown in FIG. 24 in a direction β-β.
Figure 26:
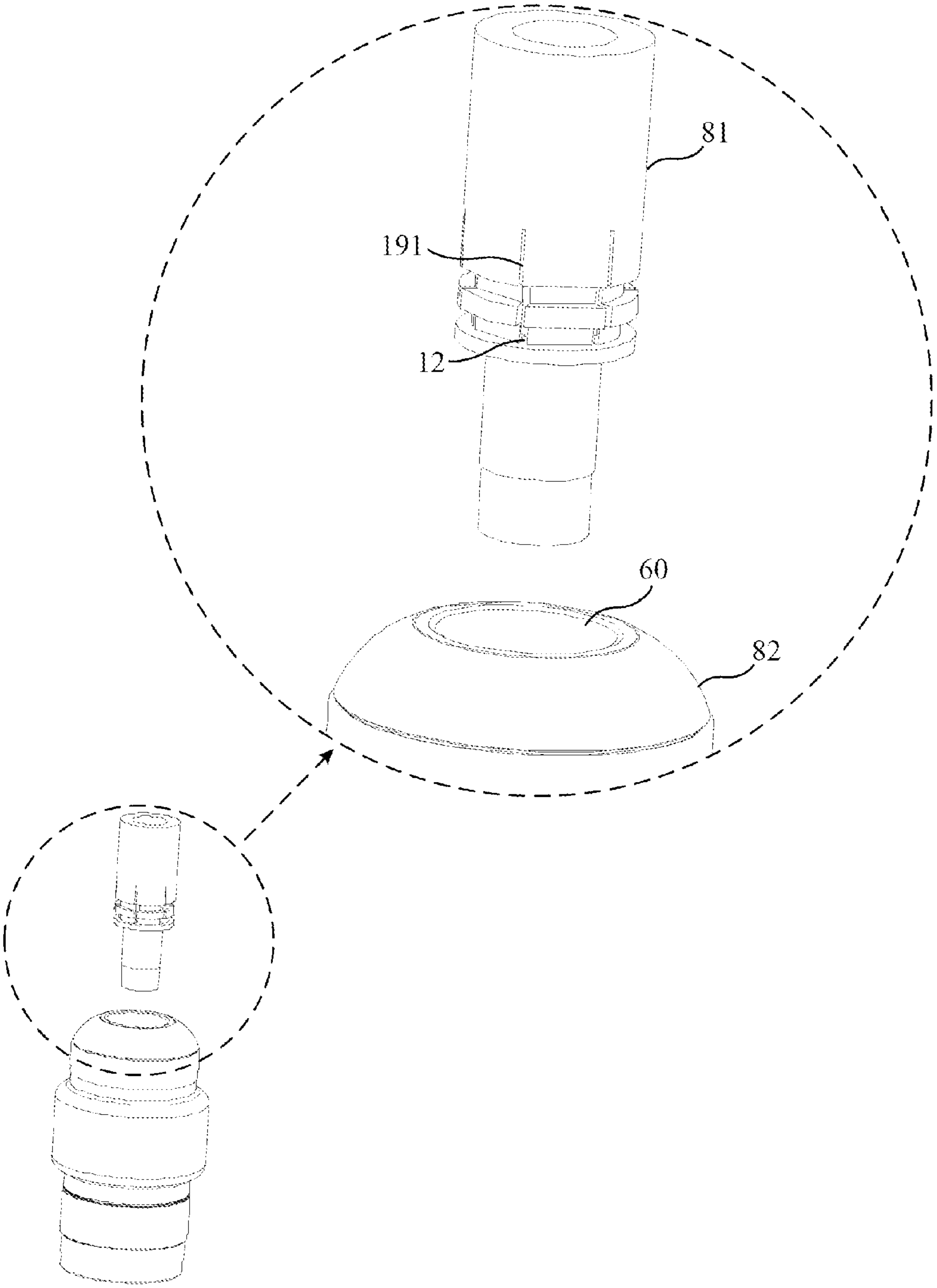
FIG. 26 is a schematic exploded structural view of the vaporizer shown in FIG. 24.

Referring to FIG. 24 to FIG. 26, FIG. 24 is a schematic structural diagram of a fifth embodiment of a vaporizer according to this application, FIG. 25 is a schematic cross-sectional structural view of the vaporizer shown in FIG. 24 in a direction β-β, and FIG. 26 is a schematic exploded structural view of the vaporizer shown in FIG. 24.

The following describes an exemplary embodiment in which an air-curtain forming structure is a vaporizer applicable to an electronic vaporization device.

In this embodiment, the air-curtain forming structure is in the form of a vaporizer. The vaporizer provided in this embodiment may be applicable to electronic vaporization devices such as an e-cigarette and a medical vaporizer. FIG. 24 to FIG. 26 show a situation in which the air-curtain forming structure is applicable to an e-cigarette, which is merely used for description and is not intended to constitute a limitation to an application environment of the air-curtain forming structure in this embodiment.

The vaporizer includes an air outlet channel insert 81 and a vapor generation device 82. The air outlet channel insert 81 is connected to the vapor generation device 82, and the vapor generation device 82 is configured to generate vapor and convey the vapor to a user through the air outlet channel insert 81 for the user to inhale.

As shown in FIG. 25, the vapor generation device 82 further includes a liquid storage cavity 50 configured to store an aerosol-generation substrate. As shown in FIG. 25, the vapor generation device 82 further includes a vaporization core 40 configured to vaporize the aerosol-generation substrate to form vapor.

For a situation that the electronic vaporization device in this embodiment is specifically an e-cigarette, the vaporization core 40 may be in a form of a porous ceramic heating body. That is, the vaporization core 40 forms a porous ceramic heating body by welding a coil on a porous ceramic, so that heat can be generated and the aerosol-generation substrate can be vaporized to form vapor. The specific principle thereof falls with the scope understood by a person skilled in the art, and details are not described herein again. Certainly, for situations in which the air-curtain forming structure is applicable to other fields, the vaporization core 40 may also be an ultrasonic vaporization sheet, which is not limited herein.

Still referring to FIG. 25 and FIG. 26, the vapor generation device 82 is provided with a mounting portion 60, and the air outlet channel insert 81 is configured to be inserted in the mounting portion 60. The air outlet channel insert 81 includes an outer wall 811, an inner wall 812, and a first air inlet channel 12. The inner wall 812 encircles to form an air outlet channel 72, the outer wall 811 is provided with a first airflow guide channel 191, and the first airflow guide channel 191 is in communication with the first air inlet channel 12 and the air outlet channel 72 respectively.

When the air outlet channel insert 81 is inserted in the mounting portion 60, the air outlet channel 72 is in communication with the vaporization core 40, and the first airflow guide channel 191 is in communication with the outside to guide an external airflow to enter the air outlet channel 72 through the first air inlet channel 12, so as to form a blocking airflow between an inner wall of the air outlet channel insert 81 and the vapor.

Further, when the air outlet channel insert 81 is inserted in the mounting portion 60, a part of the air outlet channel insert 81 is accommodated in the mounting portion 60, and a remaining part is arranged outside the mounting portion 60. As shown in FIG. 24, the first air inlet channel 12 is provided in the part of the air outlet channel insert 81 accommodated in the mounting portion 60, and the first airflow guide channel 191 extends to the part of the air outlet channel insert 81 arranged outside the mounting portion 60 to be in communication with the outside.

Further, as shown in FIG. 25, the vaporization core 40 is in a shape of a hollow cylinder, a central axis of the vaporization core 40 overlaps with a central axis of the air outlet channel insert 81, and an inner diameter W1 of an end portion of the air outlet channel 72 facing the vaporization core 40 is greater than an inner diameter W2 of the vaporization core 40.

In this embodiment, vapor generated by the vaporization core 40 vaporizing the aerosol-generation substrate is formed in a hollow region of the vaporization core 40 and can be conveyed to the air outlet channel 72 of the air outlet channel insert 81 along with an airflow, so that the vapor is outputted to a user for the user to inhale. According to the foregoing method, the blocking airflow is attached to the inner wall of the air outlet channel insert 81, the vapor conveyed from the vaporization core 40 to the air outlet channel 72 can be relatively located at a middle portion of the air outlet channel 72 under the limitation of the blocking airflow, and the blocking airflow is relatively located at an edge of the air outlet channel 72, thereby preventing the vapor from being in contact with the inner wall of the air outlet channel insert 81 as much as possible to avoid condensation. If the inner diameter of the end portion of the air outlet channel facing the vaporization core 40 is less than or equal to the inner diameter of the vaporization core 40, the vapor conveyed from the vaporization core 40 to the air outlet channel 72 may be mixed with the blocking airflow. As a result, the vapor is in contact with the inner wall of the air outlet channel insert 81 and is then condensed. The vapor is shown by an arrow G in FIG. 25, and the blocking airflow is shown by an arrow Q1 in FIG. 25.

The air outlet channel insert 81 and related specific designs are described in detail in the following embodiments.

Figure 27:
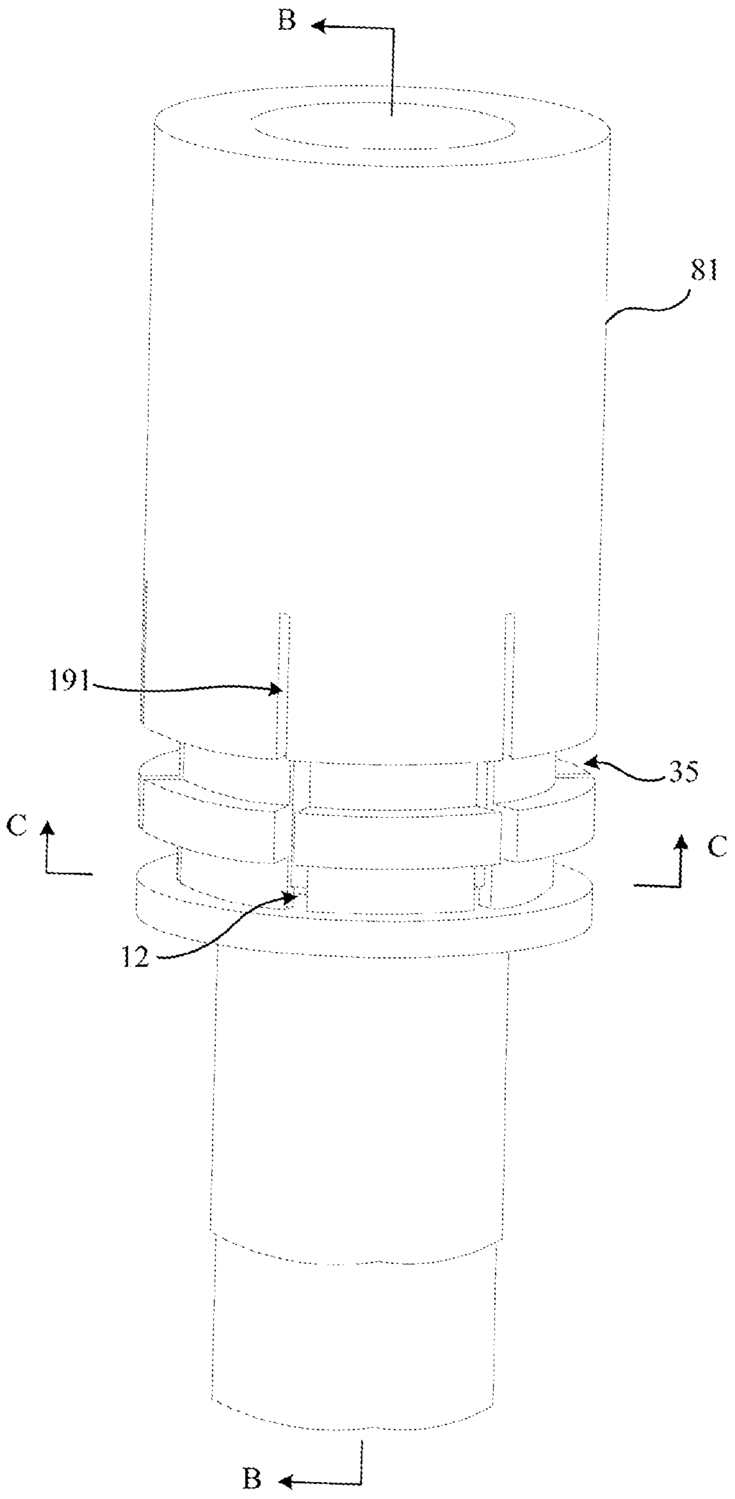
FIG. 27 is a schematic structural diagram of an embodiment of an air outlet channel insert according to this application.
Figure 28:
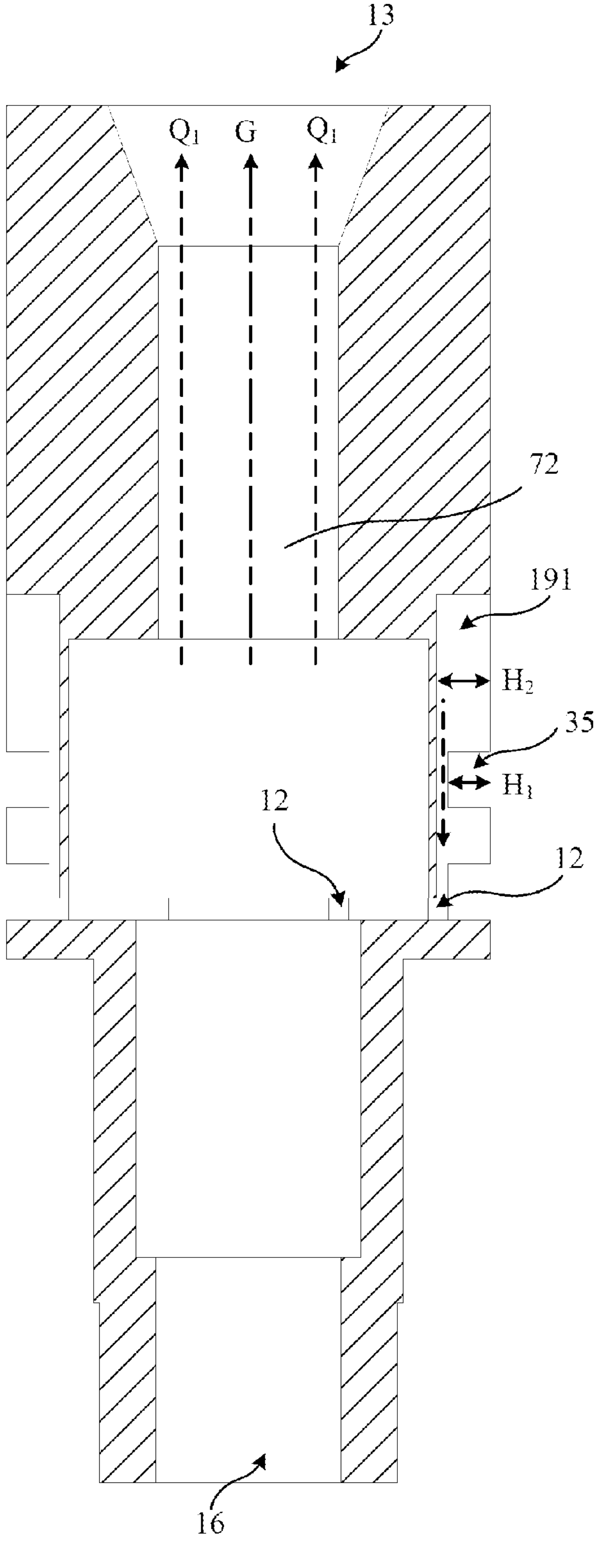
FIG. 28 is a schematic cross-sectional structural view of the air outlet channel insert shown in FIG. 27 in a direction B-B.

Referring to FIG. 27 and FIG. 28, FIG. 27 is a schematic structural diagram of an embodiment of an air outlet channel insert according to this application, and FIG. 28 is a schematic cross-sectional structural view of the air outlet channel insert shown in FIG. 27 in a direction B-B.

The following describes an exemplary embodiment in which an air-curtain forming structure is an air outlet channel insert applicable to a vaporizer.

In this embodiment, the air-curtain forming structure is in the form of an air outlet channel insert 81. The air outlet channel insert 81 provided in this embodiment may be applicable to electronic vaporization devices such as an e-cigarette, a medical vaporization electronic device, or an open-pod-system (POD) vaping device, which is not limited herein.

Optionally, the air outlet channel insert 81 includes a suction nozzle portion 813, and the user inhales vapor generated by the vaporizer through the suction nozzle portion 813. That is, the air outlet channel insert 81 in this embodiment serves as a suction nozzle part of the vaporizer. The suction nozzle portion 813 may be integrally formed on the air outlet channel insert 81, or may be separated from the air outlet channel insert 81 by adopting a detachable design, which is not limited herein.

Specifically, an air outlet channel 72 is provided inside the air outlet channel insert 81, and the air outlet channel 72 is configured to convey vapor. The air outlet channel insert 81 further includes a first air inlet channel 12, the first air inlet channel 12 is provided on a side wall of the air outlet channel insert 81 and in communication with the air outlet channel 72, and the first air inlet channel 12 is configured to introduce an external airflow into the air outlet channel 72, to form a blocking airflow between an inner wall of the air outlet channel insert 81 and the vapor (the vapor is shown by an arrow G in FIG. 28, and the blocking airflow is shown by an arrow Q1 in FIG. 28, which are the same below). The inner wall of the air outlet channel insert 81 and the vapor are blocked by the blocking airflow, so that the vapor is in contact with the inner wall of the air outlet channel insert 81 as little as possible. Therefore, the problem of vapor condensation can be alleviated, and formation of condensate can be reduced, thereby further reducing a risk of occurrence of liquid leakage and improving the use experience of a user.

The air outlet channel insert 81 further includes a first airflow guide channel 191. The first airflow guide channel 191 is provided on an outer wall of the air outlet channel insert 81, and the first airflow guide channel 191 is in communication with the first air inlet channel 12 and the outside to guide an external airflow to enter the air outlet channel 72 through the first air inlet channel 12, so as to form a blocking airflow between the inner wall of the air outlet channel insert 81 and the vapor. That is, the first airflow guide channel 191 is configured to guide an external airflow to enter the first air inlet channel 12, to ensure that the first air inlet channel 12 has a sufficient air intake amount, to further ensure an effect of a formed blocking airflow for blocking the vapor, thereby further helping alleviate the problem of vapor condensation.

Further, the air outlet channel insert 81 is further provided with a first air inlet 16 and an air outlet 13. The first air inlet 16 and the air outlet 13 are provided opposite to each other and in communication with the air outlet channel 72 respectively. Vapor enters the air outlet channel 72 through the first air inlet 16 and is conveyed to the air outlet 13 through the air outlet channel 72, and then the vapor is outputted from the air outlet 13 for the user to inhale.

The first air inlet channel 12 is provided close to the first air inlet 16, and the first airflow guide channel 191 extends toward the air outlet 13. In this way, a coverage range of the blocking airflow can be improved as much as possible. That is, to cause the blocking airflow to be formed on the end portion on which the first air inlet 16 is provided as much as possible, the blocking airflow then flows to the air outlet 13 through the air outlet channel 72, so that a blocking airflow is formed in an extending direction of the air outlet channel 72 in the air outlet channel insert 81. Therefore, contact between the vapor and the inner wall of the air outlet channel insert 81 is greatly reduced, and the problem of vapor condensation is alleviated.

Still referring to FIG. 27 and FIG. 28, in an embodiment, a periphery of the air outlet channel insert 81 is further provided with a limiting groove 35 surrounding in a circumferential direction of the air outlet channel insert, where the limiting groove 35 is configured to place an elastic ring to fix the air outlet channel insert 81 to the vapor generation device. The limiting groove 35 and the vapor generation device are described in detail in the foregoing embodiments, and details are not described herein again. In addition, the elastic ring may be a silicone ring, which is not limited herein.

As shown in FIG. 28, the limiting groove 35 is in communication with the first airflow guide channel 191, and a depth H1 of the limiting groove 35 is less than a depth H2 of the first airflow guide channel 191. In this way, a cavity with a specific volume is formed between a groove bottom of the limiting groove 35 and a bottom portion of the first airflow guide channel 191. That is, even if an elastic ring is placed in the limiting groove 35, the elastic ring may not block the cavity between the groove bottom of the limiting groove 35 and the bottom portion of the first airflow guide channel 191, to ensure that the first air inlet channel 12 has a sufficient air intake amount to form a blocking airflow. FIG. 28 shows a flow path that an airflow introduced by the first airflow guide channel 191 avoids the limiting groove 35 through the cavity.

Optionally, the depth of the first airflow guide channel 191 is preferably 0.945 mm, to ensure that the first airflow guide channel 191 can introduce sufficient airflows, so as to ensure that the first air inlet channel 12 has a sufficient air intake amount to form a blocking airflow.

Figure 29:
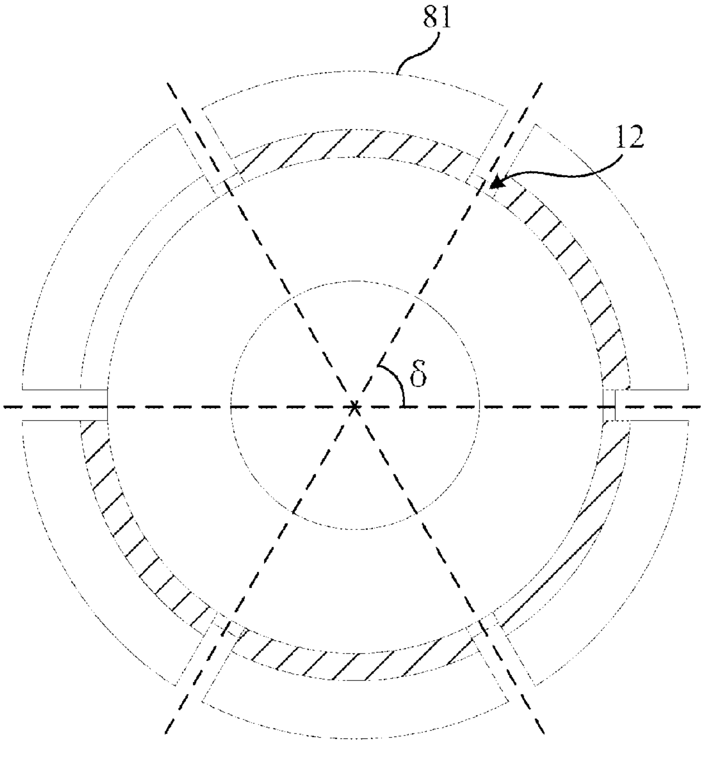
FIG. 29 is a schematic cross-sectional structural view of the air outlet channel insert shown in FIG. 27 in a direction C-C.

Referring to FIG. 27 and FIG. 29, FIG. 29 is a schematic cross-sectional structural view of the air outlet channel insert shown in FIG. 27 in a direction C-C.

In an embodiment, the air outlet channel insert includes a plurality of first air inlet channels 12, and the plurality of first air inlet channels 12 are provided at intervals sequentially in a circumferential direction of the air outlet channel insert 81. In this way, when the user performs inhalation, airflows enter the plurality of first air inlet channels 12 almost simultaneously to form blocking airflows, and the blocking airflows formed by the airflows entering through the plurality of first air inlet channels 12 form an air curtain.

Further, the first air inlet channels are provided penetrating from the outer wall 811 to the inner wall 812 of the air outlet channel insert 81, and the plurality of first air inlet channels 12 are uniformly distributed in the circumferential direction of the air outlet channel insert 81, to optimize the distribution of the blocking airflows formed by the airflows entering through the plurality of first air inlet channels 12 inside the air outlet channel insert 81, thereby further helping alleviate the problem of vapor condensation.

Still further, specific performance of that the plurality of first air inlet channels 12 are uniformly distributed in the circumferential direction of the air outlet channel insert 81 is that each of the plurality of first air inlet channels 12 extends in a radial direction of the air outlet channel insert 81 at a position thereof, and angles $\delta$ between extending directions of any two adjacent first air inlet channels 12 are the same.

For example, FIG. 29 shows that 6 first air inlet channels 12 are provided on the air outlet channel insert 81, a central axis of each of the first air inlet channels 12 passes through a center of a cross-section of the air outlet channel insert 81, and angles between extending directions of any two adjacent first air inlet channels 12 are all 60°. The central axis of the first air inlet channel 12 is parallel to the extending direction of the first air inlet channel 12, and the cross-section of the air outlet channel insert 81 is a section taken in the radial direction of the air outlet channel insert 81.

Optionally, a cross-section of the first air inlet channel 12 is preferable in a shape of a square, and specifically, may be a square whose side lengths are 0.2 mm*0.2 mm or 0.4 mm*0.4 mm, where the cross-section of the first air inlet channel 12 is a section taken in a direction perpendicular to the extending direction thereof. In addition, the number of the first air inlet channels 12 preferably ranges from 6 to 12, such as 6, 9, or 12, to ensure that the plurality of first air inlet channels 12 have a sufficient air intake amount to form blocking airflows.

Further, the outer wall 811 of the air outlet channel insert 81 is provided with a plurality of first airflow guide channels 191, and the plurality of first airflow guide channels 191 are distributed at uniform intervals in the circumferential direction of the air outlet channel insert 81, to ensure the uniformity of the air intake amount and air intake efficiency of each first air inlet channel 12 in communication with the first airflow guide channel 191 In addition, the first airflow guide channel 191 extends in a direction parallel to a central axis of the vaporizer, so that the structure of the air outlet channel insert 81 can be simplified, thereby facilitating design and production of the air outlet channel insert 81.

Figure 30:
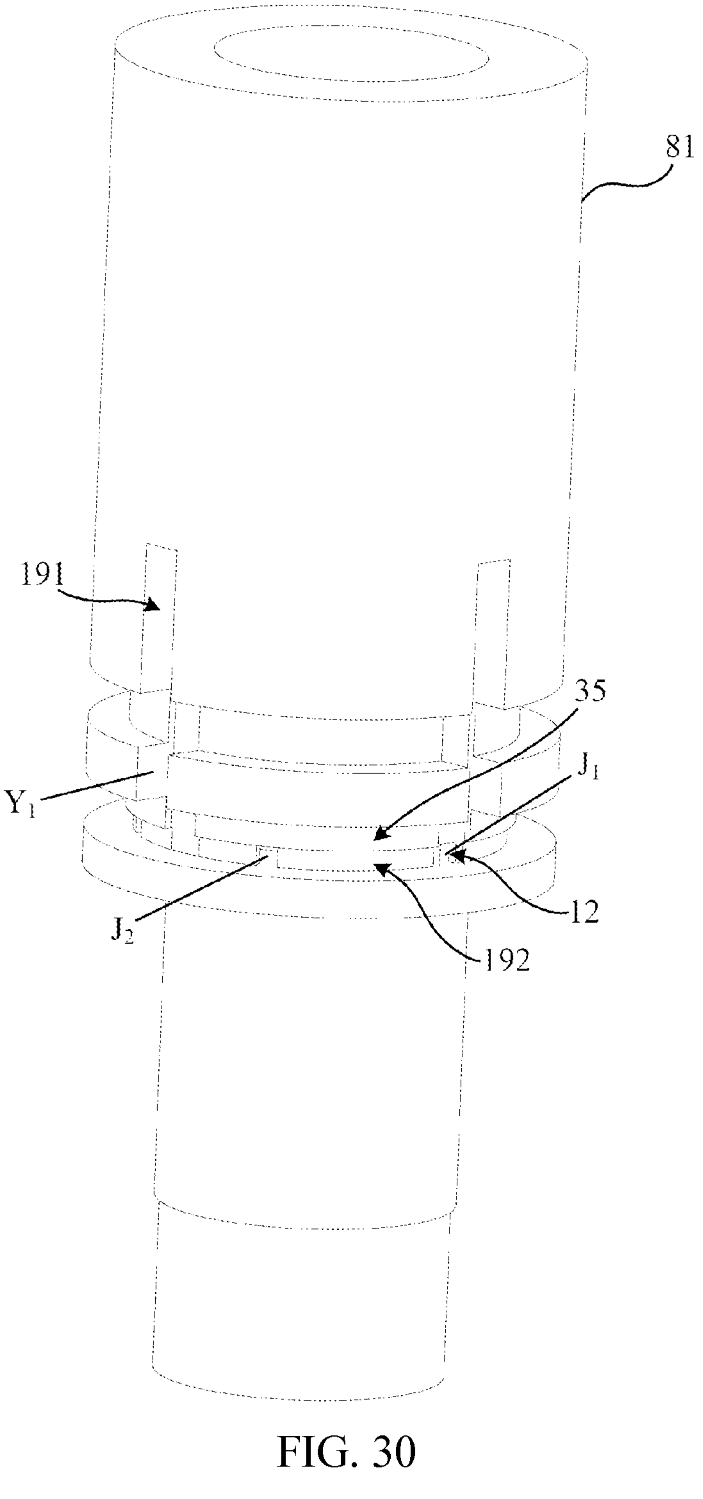
FIG. 30 is a schematic structural diagram of another embodiment of an air outlet channel insert according to this application.

Referring to FIG. 30, FIG. 30 is a schematic structural diagram of another embodiment of an air outlet channel insert according to this application.

In an embodiment, for the situation of the plurality of first air inlet channels 12 described above, a periphery of the air outlet channel insert 81 is further provided with a second airflow guide channel 192. The second airflow guide channel 192 is in communication with the first airflow guide channel 191, an extending direction of the first airflow guide channel 191 is different from an extending direction of the second airflow guide channel 192, and at least some first air inlet channels 12 are in communication with the second airflow guide channel 192.

For an air outlet channel insert 81 that is not provided with the second airflow guide channel 192, each of the first air inlet channels 12 needs to be in communication with one first airflow guide channel 191, to ensure air intake of each of the first air inlet channels 12, which means that the number of the first air inlet channels 12 is equal to the number of the first airflow guide channels 191 in this case. In this embodiment, the air outlet channel insert 81 is additionally provided with the second airflow guide channel 192, and at least some first air inlet channels 12 are in communication with the second airflow guide channel 192. In this way, airflows introduced by the first airflow guide channels 191 can be allocated to each of the first air inlet channels 12 through the second airflow guide channel 192, to ensure air intake of each of the first air inlet channels 12. Therefore, in this embodiment, it is permitted that the number of the first air inlet channels 12 is greater than the number of the first airflow guide channels 191, thereby reducing the number of the first airflow guide channels 191 and helping simplify the structure of the air outlet channel insert 81.

It may be understood that, a first air inlet channel 12 that is not in communication with the second airflow guide channel 192 needs to be in direct communication with a first airflow guide channel 191 to ensure air intake.

For example, FIG. 30 shows that some first air inlet channels 12 are in direct communication with the first airflow guide channels 191, and the remaining first air inlet channels 12 are in communication with the first air inlet channels 12 through the second airflow guide channel 192. For example, in FIG. 30, a first air inlet channel J1 is in direct communication with a first airflow guide channel 191, and a first air inlet channel J2 is not in direct communication with a first airflow guide channel 191 but in communication with a first air inlet channel 12 through the second airflow guide channel 192.

The second airflow guide channel 192 is provided surrounding in a closed manner in the circumferential direction of the air outlet channel insert 81, an entrance of the first air inlet channel 12 is provided at a bottom portion of the second airflow guide channel 192, and the second airflow guide channel 192 is preferably provided on the groove bottom of the limiting groove 35, thereby helping simplify the structure of the air outlet channel insert 81 to the greatest extent. The first air inlet channel 12 in direct communication with the first airflow guide channel 191 may implement air intake through the first airflow guide channel 191 with which the first air inlet channel is in direct communication, and the first air inlet channel 12 that is not in direct with the first airflow guide channel 191 may be in communication with the first airflow guide channel 191 through the second airflow guide channel 192 with which the first air inlet channel is in direct communication to implement air intake.

Certainly, in some other embodiments of this application, the first airflow guide channel 191 is not necessarily in direct communication with a first air inlet channel 12. For example, in FIG. 30, a first airflow guide channel Y1 is not in direct communication with a first air inlet channel 12.

FIG. 30 further shows that the periphery of the air outlet channel insert 81 is provided with two limiting grooves 35 distributed at intervals in an axial direction thereof, and the first air inlet channel 12 and the second airflow guide channel 192 are provided at a position of the limiting groove 35 that is closest to the first air inlet 16, to improve the coverage range of the blocking airflow. Certainly, in some other embodiments of this application, the first air inlet channel 12 and the second airflow guide channel 192 may also be provided at a position of the limiting groove 35 that is relatively away from the first air inlet 16, which is not limited herein.

In addition, FIG. 30 further shows that the second airflow guide channel 192 only includes a channel section extending in the circumferential direction of the air outlet channel insert 81. In some other embodiments of this application, the second airflow guide channel 192 may further include a channel section extending in the axial direction of the air outlet channel insert 81. For example, the first air inlet channel 12 is provided at the position of the limiting groove 35 that is relatively close to the first air inlet 16. When the channel section of the second airflow guide channel 192 extending in the circumferential direction of the air outlet channel insert 81 is arranged at the position of the limiting groove 35 that is relatively away from the first air inlet 16, the first air inlet channel 12 and the channel section of the second airflow guide channel 192 extending in the circumferential direction of the air outlet channel insert 81 need to be in communication with each other through the channel section of the second airflow guide channel 192 extending in the axial direction of the air outlet channel insert 81.

Figure 31:
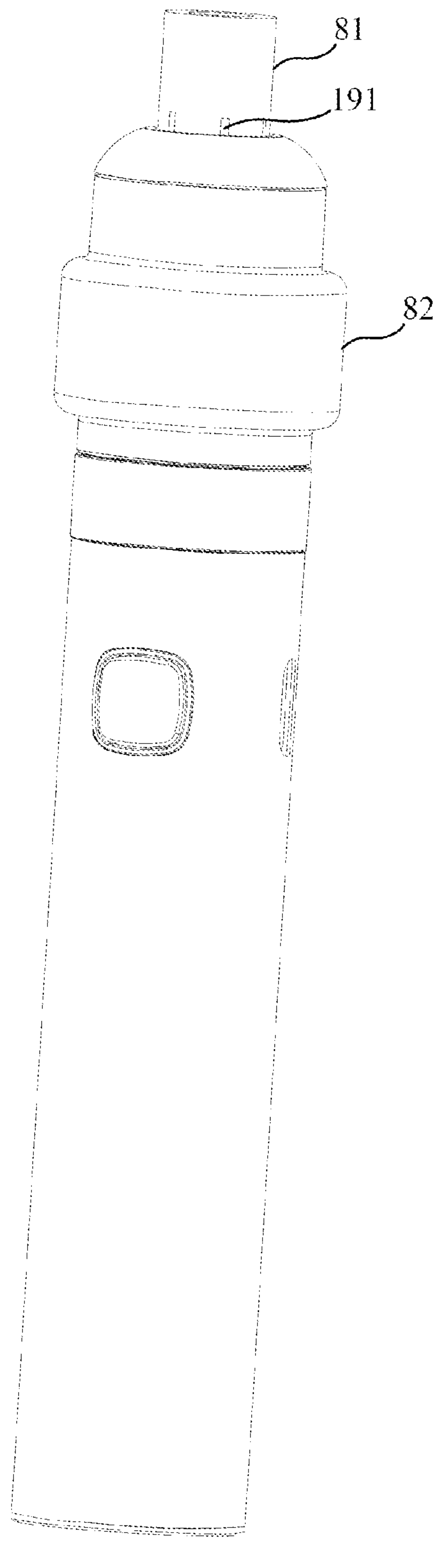
FIG. 31 is a schematic structural diagram of a first embodiment of an electronic vaporization device according to this application.
Figure 32:
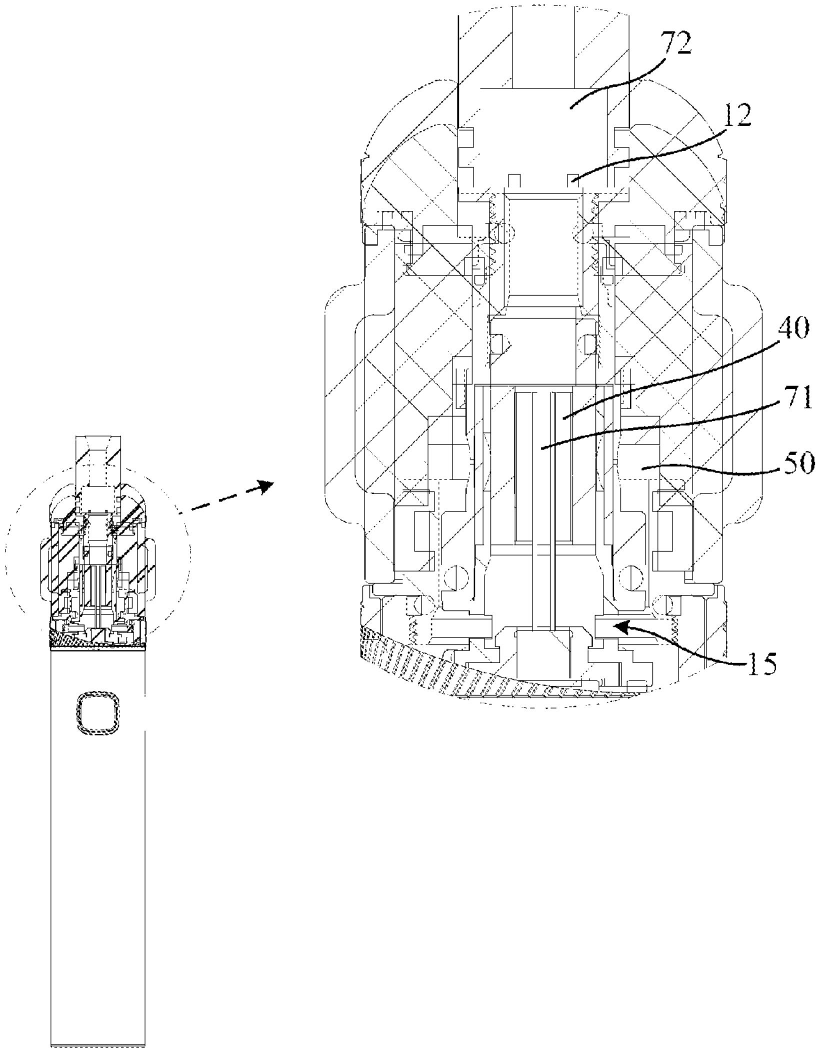
FIG. 32 is a schematic partial cross-sectional structural view of the electronic vaporization device shown in FIG. 31.

Referring to FIG. 31 and FIG. 32, FIG. 31 is a schematic structural diagram of a first embodiment of an electronic vaporization device according to this application, and FIG. 32 is a schematic partial cross-sectional structural view of the electronic vaporization device shown in FIG. 31.

The following describes an exemplary embodiment of an electronic vaporization device to which the air outlet channel insert described in the foregoing embodiments are applicable.

In this embodiment, the electronic vaporization device includes an air outlet channel insert 81 and a vapor generation device 82. The air outlet channel insert 81 is connected to the vapor generation device 82, and the vapor generation device 82 is configured to generate vapor and convey the vapor to a user through the air outlet channel insert 81 for the user to inhale.

Specifically, the vapor generation device 82 includes a vaporization cavity 71. A vaporization core 40 is arranged in the vaporization cavity 71 and configured to vaporize an aerosol-generation substrate to form vapor. The vaporization cavity 71 is in communication with the air outlet channel 72 of the air outlet channel insert 81. The vapor generation device 82 further includes a liquid storage cavity 50 configured to store an aerosol-generation substrate.

For a situation that the electronic vaporization device in this embodiment is specifically an e-cigarette, the vaporization core 40 may be in a form of a porous ceramic heating body. That is, the vaporization core 40 forms a porous ceramic heating body by welding a coil on a porous ceramic, so that heat can be generated and the aerosol-generation substrate can be vaporized to form vapor. The specific principle thereof falls with the scope understood by a person skilled in the art, and details are not described herein again. Certainly, for situations in which the air-curtain forming structure is applicable to other fields, the vaporization core 40 may also be an ultrasonic vaporization sheet, which is not limited herein.

The vaporization cavity 71 is further provided with a second air inlet channel 15. When the user performs inhalation, an external airflow enters the vaporization cavity 71 through the second air inlet channel 15, at the same time, the vaporization core 40 is configured to vaporize the aerosol-generation substrate stored in the liquid storage cavity 50 to generate vapor, and the airflow entering through the second air inlet channel 15 carries the vapor in the vaporization cavity 71 to be discharged through the air outlet channel 72, which can speed up discharging of the vapor. Therefore, contact between the vapor and the inner wall of the vaporization cavity 71 and contact between the vapor and the inner wall of the air outlet channel 72 can be reduced to some extent, and the problem of vapor condensation can also be alleviated.

An air outlet channel 72 is provided inside the air outlet channel insert 81, and the air outlet channel 72 is configured to convey vapor. The air outlet channel insert 81 further includes a first air inlet channel 12, the first air inlet channel 12 is provided on a side wall of the air outlet channel insert 81 and in communication with the air outlet channel 72, and the first air inlet channel 12 is configured to introduce an external airflow into the air outlet channel 72, to form a blocking airflow between an inner wall of the air outlet channel insert 81 and the vapor. The inner wall of the air outlet channel insert 81 and the vapor are blocked by the blocking airflow, so that the vapor is in contact with the inner wall of the air outlet channel insert 81 as little as possible. Therefore, the problem of vapor condensation can be alleviated, and formation of condensate can be reduced, thereby further reducing a risk of occurrence of liquid leakage and improving the use experience of a user.

The air outlet channel insert 81 further includes a first airflow guide channel 191. The first airflow guide channel 191 is provided on an outer wall of the air outlet channel insert 81, and the first airflow guide channel 191 is in communication with the first air inlet channel 12 and the outside to guide an external airflow to enter the air outlet channel 72 through the first air inlet channel 12, so as to form a blocking airflow between the inner wall of the air outlet channel insert 81 and the vapor. That is, the first airflow guide channel 191 is configured to guide an external airflow to enter the first air inlet channel 12, to ensure that the first air inlet channel 12 has a sufficient air intake amount, to further ensure an effect of a formed blocking airflow for blocking the vapor, thereby further helping alleviate the problem of vapor condensation.

It should be noted that, in this embodiment, the air outlet channel insert 81 including the first airflow guide channel 191 has been described in detail in the foregoing embodiments, and details are not described herein again.

Figure 33:
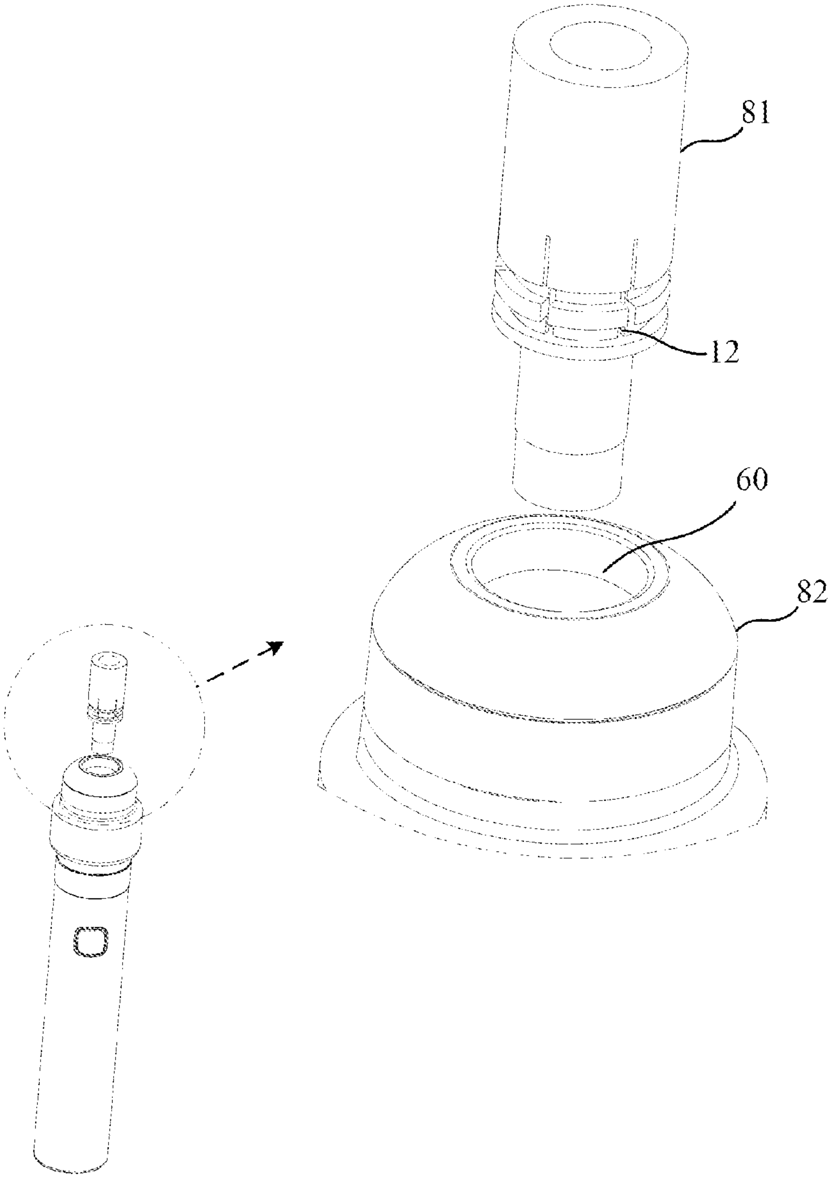
FIG. 33 is a schematic exploded structural view of the electronic vaporization device shown in FIG. 31.

Referring to FIG. 33, FIG. 33 is a schematic exploded structural view of the electronic vaporization device shown in FIG. 31.

In an embodiment, the vapor generation device 82 is provided with a mounting portion 60, and the air outlet channel insert 81 is inserted in the mounting portion 60. The first air inlet channel 12 is provided in a part of the air outlet channel insert 81 arranged outside the mounting portion 60. In this way, a coverage range of the blocking airflow can be improved as much as possible, so that a blocking airflow is formed in an extending direction of the air outlet channel 72 in the air outlet channel insert 81. Therefore, contact between the vapor and the inner wall of the air outlet channel insert 81 is greatly reduced, and the problem of vapor condensation is alleviated.

In addition, the entrance of the first air inlet channel 12 is exposed to the periphery of the air outlet channel insert 81, the periphery of the air outlet channel insert 81 is further provided with a first airflow guide channel 191, and the first airflow guide channel 191 is in communication with the entrance of the first air inlet channel 12 and extends to the outside of the mounting portion 60, so that the first air inlet channel 12 can be in communication with the outside, to further ensure that an external airflow can enter the first air inlet channel 12 along with an inhalation action of the user and is used to form a blocking airflow.

Further, a bottom portion of the air outlet channel insert 81 is inserted in the mounting portion 60, and the first air inlet channel 12 is provided in the bottom portion of the air outlet channel insert 81, so that the coverage range of the blocking airflow can be improved as much as possible, to ensure that a blocking airflow is formed in the extending direction of the air outlet channel 72 in the air outlet channel insert 81 to the greatest extent, thereby reducing contact between the vapor and the inner wall of the air outlet channel insert 81 to the greatest extent and alleviating the problem of vapor condensation.

For the electronic vaporization device provided in this embodiment, parametric simulation analysis is performed on situations that the number of the first air inlet channels 12 is 6, 9, and 12 respectively, to explore changes, namely, change situations of parameters in an airway along with the number of the first air inlet channels 12.

Figure 34:
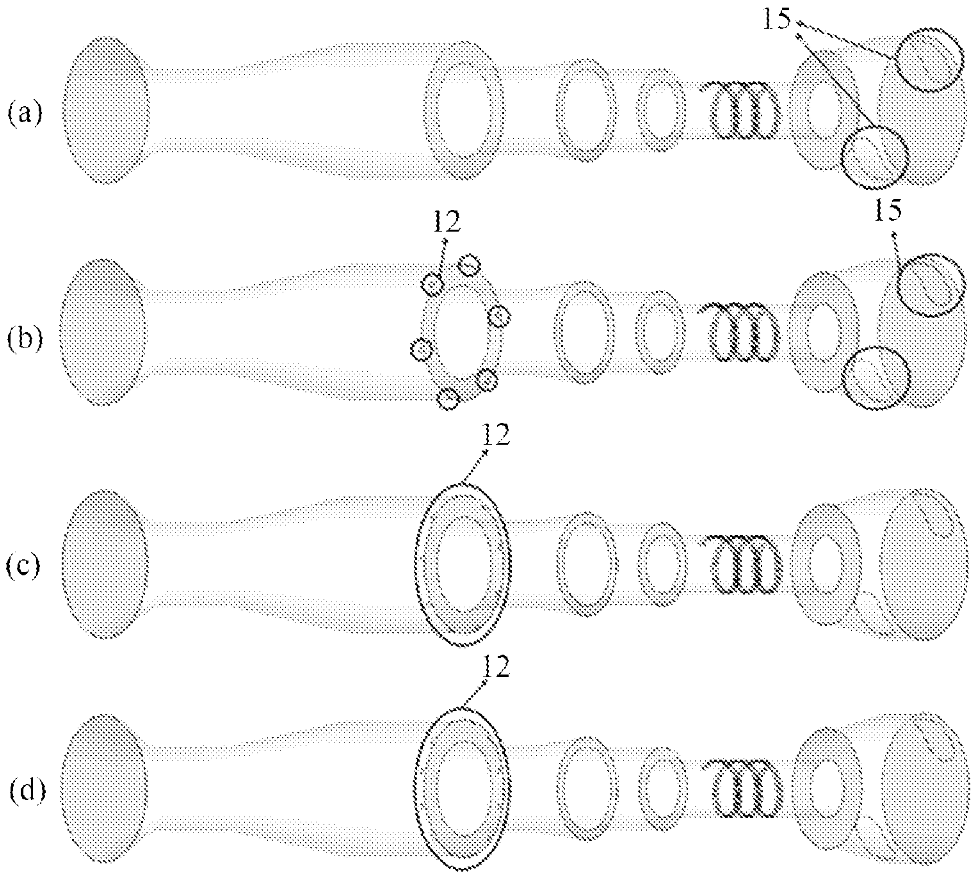
FIG. 34 is a schematic diagram of a simulation structure of electronic vaporization devices having different numbers of first air inlet channels according to this application.

FIG. 34*a* shows a simulation structure of a conventional electronic vaporization device corresponding to a situation that no first air inlet channel 12 is provided; FIG. 34*b* shows a simulation structure of an electronic vaporization device corresponding to a situation that the number of the first air inlet channels 12 is 6; FIG. 34*c* shows a simulation structure of an electronic vaporization device corresponding to a situation that the number of the first air inlet channels 12 is 9; and FIG. 34*d* shows a simulation structure of an electronic vaporization device corresponding to a situation that the number of the first air inlet channels 12 is 12.

The results are shown in the following table. A basic example corresponds to the situation that the number of the first air inlet channels 12 is zero, namely, corresponds to the conventional electronic vaporization device that is not provided with the first air inlet channel 12; a first test example corresponds to the situation that the number of the first air inlet channels 12 is 6; a second test example corresponds to the situation that the number of the first air inlet channels 12 is 9; and a third test example corresponds to the situation that the number of the first air inlet channels 12 is 12. In addition, a cross-section of the first air inlet channel 12 is in a shape of a 0.2 mm*0.2 mm square.

| | Average flow rate of air outlet (m/s) | Average temperature of air outlet (° C.) | Highest temperature of air outlet (° C.) | Amount of condensate (mg) | Total mass flow of second air inlet channel (mg/s) | Total mass flow of first air inlet channel (mg/s) | Mass flow of air outlet (mg/s) |
|---|---|---|---|---|---|---|---|
| Basic example | 1.80 | 75.12 | 109.17 | 13.73e−5 | 21.02 | 0 | 29.02 |
| First test example | 2.05 | 72.20 | 105.25 | 9.41e−5 | 20.88 | 4.035 | 32.92 |
| Second test example | 2.13 | 70.79 | 103.48 | 8.54e−5 | 20.81 | 5.958 | 34.77 |
| Third test example | 2.22 | 69.87 | 101.59 | 6.70e−5 | 20.80 | 7.849 | 36.65 |

As can be seen from the above, a specific turbulence flow is generated first due to mutual effect between the airflow entering through the first air inlet channel 12 and the vapor, which prompts mixing of air and the vapor, significantly changes volume fraction distribution of the vapor in the airway, and is presented as that most vapor is concentrated in a middle portion and is uniformly distributed in the airway. In addition, the blocking airflow causes the vapor to be away from the inner wall of the electronic vaporization device as much as possible, thereby alleviating the problem of vapor condensation and reducing formation of condensate. For example, compared with the basic example, the amount of condensate in the third test example is reduced by approximately 51.1%.

With an increase in the number of the first air inlet channels 12, a total amount of air entering the electronic vaporization device is increased, a flow rate of the airflow at the air outlet 13 is increased, and a temperature of the airflow at the air outlet 13 is reduced, so that the user does not feel too hot, thereby helping improve the taste and helping improve the use experience of the user.

Figure 35:
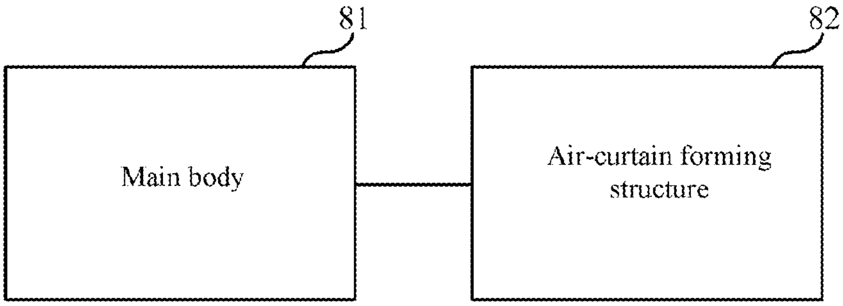
FIG. 35 is a schematic structural diagram of a second embodiment of an electronic vaporization device according to this application.

Referring to FIG. 35, FIG. 35 is a schematic structural diagram of a second embodiment of an electronic vaporization device according to this application.

In this embodiment, the electronic vaporization device may be an e-cigarette or a medical vaporization electronic device and includes a main body 91 and an air-curtain forming structure 92, where the main body 91 is connected to the air-curtain forming structure 92, the air-curtain forming structure 92 includes an airflow channel, and the airflow channel is configured to convey vapor. The air-curtain forming structure 92 further includes a first air inlet channel. The first air inlet channel is in communication with the airflow channel, and the first air inlet channel is configured to introduce an external airflow into the airflow channel, to form a blocking airflow between an inner wall of the airflow channel and the vapor.

The air-curtain forming structure 92 has been described in detail in the foregoing embodiments, and details are not described herein again.

It should be noted that, the main body 91 is defined as a set of other elements of the electronic vaporization device other than the air-curtain forming structure 92. Specifically, when the air-curtain forming structure 92 is a vaporization suction nozzle applicable to the electronic vaporization device, the main body 91 includes a main unit (including a power supply and a circuit part of the electronic vaporization device) of the electronic vaporization device and other elements (including a vaporization core) of a vaporizer other than the vaporization suction nozzle. When the air-curtain forming structure 92 is a vaporizer applicable to the electronic vaporization device, the main body 91 includes the main unit of the electronic vaporization device.

Figure 36:
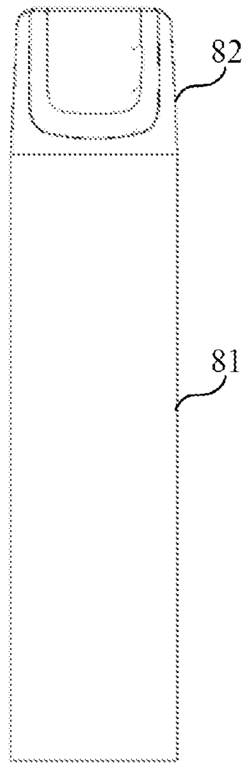
FIG. 36 is a schematic structural diagram of a third embodiment of an electronic vaporization device according to this application.

For example, FIG. 36 shows an entire form of the device, that is, the electronic vaporization device, with the main body 91 and the air-curtain forming structure 92 being assembled.

Figure 37:
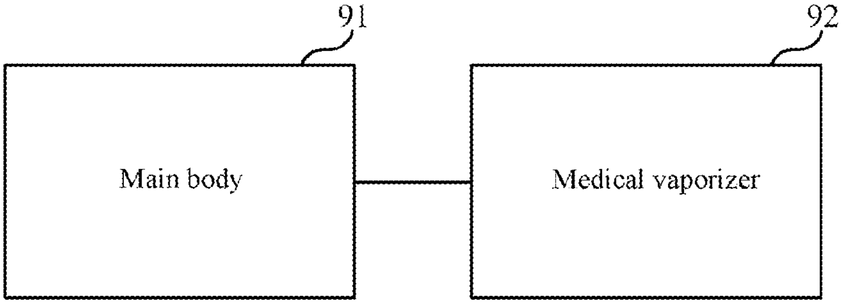
FIG. 37 is a schematic structural diagram of an embodiment of a medical vaporization electronic device according to this application.

Referring to FIG. 37, FIG. 37 is a schematic structural diagram of an embodiment of a medical vaporization electronic device according to this application.

In this embodiment, the medical vaporization electronic device is applicable to the field of medical vaporization and includes a main unit 93 (including a power supply and a circuit part of the medical vaporization electronic device) and a medical vaporizer 94 connected to the main unit 93. The medical vaporizer 94 includes a vaporization suction nozzle, and the vaporization suction nozzle is provided with a first air inlet, a second air inlet, and an air outlet. The medical vaporizer 94 further includes a liquid storage cavity, and the liquid storage cavity is configured to store an aerosol-generation substrate. The medical vaporizer 94 further includes a vaporization core. The vaporization core is arranged in the first air inlet and is configured to vaporize the aerosol-generation substrate to form vapor. The medical vaporizer 94 further includes an airflow guide member, where the airflow guide member is arranged in the vaporization suction nozzle and is in communication with the second air inlet, and the airflow guide member is configured to guide an airflow entering through the second air inlet to flow toward the vaporization core, to carry the vapor to be outputted from the air outlet.

The medical vaporizer 94 has been described in detail in the foregoing embodiments, and details are not described herein again.

Figure 38:
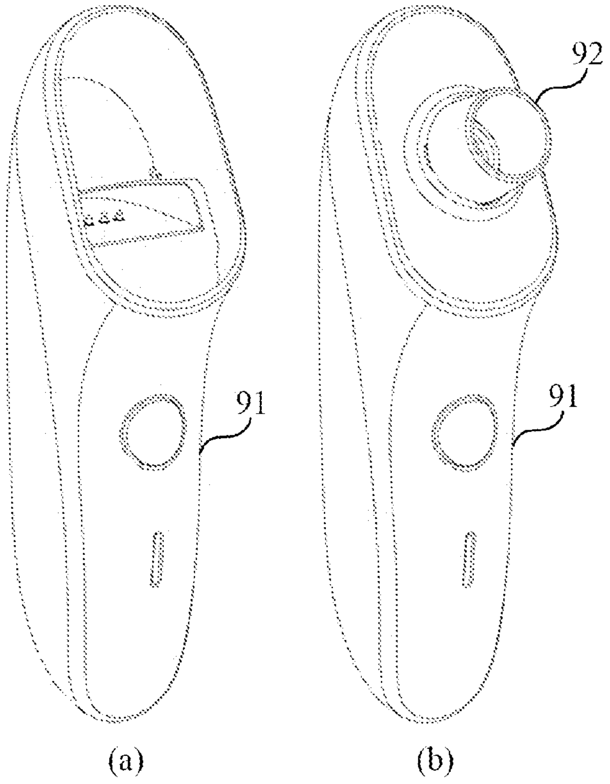
FIG. 38 is a schematic structural diagram of another embodiment of a medical vaporization electronic device according to this application.

For example, FIG. 38*a* shows an exemplary embodiment of the main unit 93, and FIG. 38*b* shows an entire form of the device, that is, the medical vaporization electronic device, with the main unit 93 and the medical vaporizer 94 being assembled.

In addition, in this application, unless otherwise explicitly specified or defined, the terms such as "connect", "connection", and "stack" should be understood in a broad sense. For example, the connection may be a fixed connection, a detachable connection, or an integral connection; a direct connection, an indirect connection through an intermediate, or internal communication between two elements or an interaction relationship between two elements. A person of ordinary skill in the art may understand the specific meanings of the foregoing terms in this application according to specific situations.

Finally, it should be noted that the foregoing embodiments are merely used for describing the technical solutions of this application, but are not intended to limit this application. Although this application is described in detail with reference to the foregoing embodiments, a person of ordinary skill in the art should understand that, modifications may still be made to the technical solutions in the foregoing embodiments, or equivalent replacements may be made to some or all of the technical features; and these modifications or replacements will not cause the essence of corresponding technical solutions to depart from the scope of the technical solutions in the embodiments of this application.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A vaporizer, comprising:

a vapor generation device comprising a liquid storage cavity, a vaporization core, and a mounting portion, the liquid storage cavity being configured to store an aerosol-generation substrate, and the vaporization core being configured to vaporize the aerosol-generation substrate to generate vapor; and an air outlet channel insert configured to be inserted in the mounting portion, the air outlet channel insert comprising an outer wall, an inner wall, and a first air inlet channel, the inner wall encircling to form an air outlet channel, the outer wall being provided with a first airflow guide channel, and the first airflow guide channel being in communication with the first air inlet channel and the air outlet channel, respectively, wherein, when the air outlet channel insert is inserted in the mounting portion, the air outlet channel is in communication with the vaporization core, and the first airflow guide channel is in communication with outside air to guide an external airflow to enter the air outlet channel through the first air inlet channel so as to form a blocking airflow between the inner wall of the air outlet channel insert and the vapor.

2. The vaporizer of claim 1, wherein the first air inlet channel is provided penetrating from the outer wall to the inner wall, wherein the air outlet channel insert comprises a plurality of first air inlet channels, and wherein the plurality of first air inlet channels are distributed at uniform intervals in a circumferential direction of the air outlet channel insert.

3. The vaporizer of claim 2, wherein each of the plurality of first air inlet channels extends in a radial direction of the air outlet channel insert at a position thereof, and wherein angles between extending directions of any two adjacent first air inlet channels are the same.

4. The vaporizer of claim 1, wherein, when the air outlet channel insert is inserted in the mounting portion, a part of the air outlet channel insert is accommodated in the mounting portion, a remaining part is arranged outside the mounting portion, the first air inlet channel is provided in a part of the air outlet channel insert accommodated in the mounting portion, and the first airflow guide channel extends to a part of the air outlet channel insert arranged outside the mounting portion to be in communication with the outside air.

5. The vaporizer of claim 1, wherein the outer wall is provided with a plurality of first airflow guide channels, and wherein the plurality of first airflow guide channels are distributed at uniform intervals in a circumferential direction of the air outlet channel insert.

6. The vaporizer of claim 1, wherein the first airflow guide channel extends in a direction parallel to a central axis of the vaporizer.

7. The vaporizer of claim 1, wherein the vaporization core comprises a hollow cylinder, wherein a central axis of the vaporization core overlaps with a central axis of the air outlet channel insert, and wherein an inner diameter of an end portion of the air outlet channel facing the vaporization core is greater than an inner diameter of the vaporization core.

8. The vaporizer of claim 1, wherein the air outlet channel insert comprises a suction nozzle portion.

9. An air outlet channel insert applicable to a vaporizer, the air outlet channel insert comprising:

an air outlet channel provided inside the air outlet channel insert and configured to convey vapor;

a first air inlet channel provided on a side wall of the air outlet channel insert and in communication with the air outlet channel; and a first airflow guide channel provided on an outer wall of the air outlet channel insert, wherein the air outlet channel insert is configured to be inserted into a mounting portion of the vaporizer, and wherein, when the air outlet channel insert is inserted in the mounting portion, the first airflow guide channel is in communication with the first air inlet channel and outside air to guide an external airflow to enter the air outlet channel through the first air inlet channel so as to form a blocking airflow between an inner wall of the air outlet channel insert and the vapor.

10. The air outlet channel insert of claim 9, further comprising:

a first air inlet; and an air outlet, wherein the first air inlet and the air outlet are in communication with the air outlet channel, respectively, wherein the first air inlet channel is provided close to the first air inlet, and wherein the first airflow guide channel extends toward the air outlet.

11. The air outlet channel insert of claim 10, wherein a periphery of the air outlet channel insert is further provided with a limiting groove surrounding in a circumferential direction of the air outlet channel insert, wherein the limiting groove is configured to place an elastic ring to fix the air outlet channel insert to a vapor generation device, wherein the limiting groove is in communication with the first airflow guide channel, and wherein a depth of the limiting groove is smaller than a depth of the first airflow guide channel.

12. The air outlet channel insert of claim 9, further comprising:

a plurality of first air inlet channels, wherein a periphery of the air outlet channel insert is provided with a second airflow guide channel, the second airflow guide channel being in communication with the first airflow guide channel, an extending direction of the first airflow guide channel being different from an extending direction of the second airflow guide channel, wherein at least some first air inlet channels are in communication with the second airflow guide channel, and wherein a number of the first air inlet channels is greater than a number of the first airflow guide channels.

13. The air outlet channel insert of claim 12, wherein the second airflow guide channel is provided surrounding in a closed manner in a circumferential direction of the air outlet channel insert, and wherein an entrance of the first air inlet channel is provided at a bottom portion of the second airflow guide channel.

14. The air outlet channel insert of claim 9, wherein the outer wall is provided with a plurality of first airflow guide channels, and wherein the plurality of first airflow guide channels are distributed at uniform intervals in a circumferential direction of the air outlet channel insert.

15. The air outlet channel insert of claim 9, wherein the first airflow guide channel extends in a direction parallel to a central axis of the air outlet channel insert.

16. The air outlet channel insert of claim 9, wherein the air outlet channel insert comprises a plurality of first air inlet channels, and wherein the plurality of first air inlet channels are provided at intervals sequentially in a circumferential direction of the air outlet channel insert.

17. The air outlet channel insert of claim 16, wherein the plurality of first air inlet channels are uniformly distributed in the circumferential direction of the air outlet channel insert.

18. The air outlet channel insert of claim 17, wherein each of the plurality of first air inlet channels extends in a radial direction of the air outlet channel insert at a position thereof, and wherein angles between extending directions of any two adjacent first air inlet channels are the same.

19. An electronic vaporization device, comprising:

an air outlet channel insert and a vapor generation device, the air outlet channel insert being connected to the vapor generation device, wherein the air outlet channel insert comprises:

an air outlet channel provided inside the air outlet channel insert and configured to convey vapor generated by the vapor generation device;

a first air inlet channel provided on a side wall of the air outlet channel insert and in communication with the air outlet channel; and a first airflow guide channel provided on an outer wall of the air outlet channel insert, wherein the first airflow guide channel is in communication with the first air inlet channel and outside air to guide an external airflow to enter the air outlet channel through the first air inlet channel so as to form a blocking airflow between the inner wall of the air outlet channel insert and the vapor.

20. The electronic vaporization device of claim 19, wherein the vapor generation device is provided with a mounting portion, wherein the air outlet channel insert is inserted in the mounting portion, wherein the first air inlet channel is provided in a part of the air outlet channel insert arranged in the mounting portion, and wherein the first airflow guide channel extends outside the mounting portion so that the first air inlet channel is in communication with the outside air.

* * * * *